(12) United States Patent
Wolfe et al.

(10) Patent No.: US 12,168,059 B2
(45) Date of Patent: Dec. 17, 2024

(54) TRIMERIC PEPTIDES FOR ANTISENSE DELIVERY

(71) Applicants: Sarepta Therapeutics, Inc., Cambridge, MA (US); Massachusetts Institute of Technology, Cambridge, MA (US)

(72) Inventors: Justin Wolfe, Cambridge, MA (US); Colin M. Fadzen, Cambridge, MA (US); Bradley L. Pentelute, Cambridge, MA (US); Gunnar J. Hanson, Cambridge, MA (US)

(73) Assignees: Sarepta Therapeutics, Inc., Cambridge, MA (US); Massachusetts Institute of Technology, Cambridge, MD (US)

( * ) Notice: Subject to any disclaimer, the term of this patent is extended or adjusted under 35 U.S.C. 154(b) by 793 days.

(21) Appl. No.: 17/264,163

(22) PCT Filed: Jul. 29, 2019

(86) PCT No.: PCT/US2019/043920
§ 371 (c)(1),
(2) Date: Jan. 28, 2021

(87) PCT Pub. No.: WO2020/028254
PCT Pub. Date: Feb. 6, 2020

(65) Prior Publication Data
US 2021/0290772 A1    Sep. 23, 2021

Related U.S. Application Data

(60) Provisional application No. 62/711,894, filed on Jul. 30, 2018.

(51) Int. Cl.
*A61K 47/64* (2017.01)
*A61K 47/54* (2017.01)
*C12N 15/113* (2010.01)

(52) U.S. Cl.
CPC ........ *A61K 47/6455* (2017.08); *A61K 47/549* (2017.08); *C12N 15/113* (2013.01); *C12N 2310/11* (2013.01); *C12N 2310/3233* (2013.01); *C12N 2310/3513* (2013.01)

(58) Field of Classification Search
None
See application file for complete search history.

(56) References Cited

U.S. PATENT DOCUMENTS

| 9,161,948 B2 | 10/2015 | Hanson | |
|---|---|---|---|
| 2012/0289457 A1 | 11/2012 | Hanson | |
| 2016/0237426 A1* | 8/2016 | Hanson | A61P 31/16 |

FOREIGN PATENT DOCUMENTS

| JP | 2014-515762 A | 7/2014 | |
|---|---|---|---|
| WO | WO 2012/150960 A1 | 11/2012 | |
| WO | WO 2015/069665 A1 | 5/2015 | |
| WO | WO-2016187425 A1 * | 11/2016 | A61K 47/18 |

OTHER PUBLICATIONS

Extended European Search Report for International Application No. PCT/US2019/043920, mailed Apr. 20, 2022, 6 pages.
International Preliminary Report on Patentability for International Application No. PCT/US2019/043920, mailed Feb. 2, 2021, 6 pages.
International Search Report for International Application No. PCT/US2019/043920, mailed Dec. 4, 2019, 5 pages.
Saleh et al., "Synthesis and Splice-Redirecting Activity of Branched, Arginine-Rich Peptide Dendrimer Conjugates of Peptide Nucleic Acid Oligonucleotides", *Bioconjugate* 21:1902-1911 (2010).
Yin et al., "Context Dependent Effects of Chimeric Peptide Morpholino Conjugates Contribute to Dystrophin Exon-skipping Efficiency", *Molecular Therapy—Nucleic Acids* 2:e124 (2013).

* cited by examiner

*Primary Examiner* — Sergio Coffa
(74) *Attorney, Agent, or Firm* — Sterne, Kessler, Goldstein & Fox P.L.L.C.

(57) ABSTRACT

Provided herein are oligonucleotides, trimeric peptides, and peptide-oligonucleotide-conjugates. Also provided herein are methods of treating a muscle disease in a subject in need thereof, comprising administering to the subject oligonucleotides, trimeric peptides, and peptide-oligonucleotide-conjugates described herein.

23 Claims, 11 Drawing Sheets
Specification includes a Sequence Listing.

Reaction 1

Reaction 2

Reaction 3

Module 1

| PMO | Sequence |
|---|---|
| IVS2-654 | GCTATTACCTTAACCCAG |

Module 2

| Peptide 1 | Sequence |
|---|---|
| Penetratin | RQIKIWFQNRRMKWKK |
| pVEC | LLIILRRRIRKQAHAHSK |
| TP10 | AGYLLGKINLKALAALAKKIL |
| DPV6 | GRPRESGKKRKRKRLKP |

Module 3

| Peptide 2 | Sequence |
|---|---|
| KRVK (NLS) | KRVK |
| SV40 (NLS) | PKKKRKV |
| AAV-PHP.eB | SDGTLAVPFKA |

Module 4

| Peptide 3 | Sequence |
|---|---|
| Bpep | RXRRBRRXRRBR |
| DPV6 | GRPRESGKKRKRKRLKP |
| PPC3 | KKYRGRKRHPR |

*Fig. 3*

SEQUENCE LISTING

<160> NUMBER OF SEQ ID NOS: 56

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Arg Pro Arg Glu Ser Gly Lys Lys Arg Lys Arg Lys Arg Leu Lys
1               5                   10                  15

Pro

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Tyr Arg Gly Arg Lys Arg His Pro Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Arg Lys Ala Ala Arg Ala Pro Gly Arg Arg Lys Gln
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Arg Arg Arg Arg Arg Arg Arg Arg Arg Arg Arg
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Arg Arg Arg Arg Arg Arg Arg Arg Arg Arg Arg Arg Cys
1               5                   10

<210> SEQ ID NO 6
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 6

Cys Arg Arg Arg Arg Arg Arg Cys Arg Arg Arg Arg
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Arg Arg Arg Cys Arg Arg Arg Arg Arg Arg Cys
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Arg Arg Arg Arg Arg Arg Cys Arg Arg Arg Arg Arg Cys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Arg Arg Arg Arg Arg Arg Cys Cys Arg Arg Arg Arg Arg Cys
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (5)..(5)
<223> OTHER INFORMATION: Beta-alanine
<220> FEATURE:
<221> NAME/KEY: MOD_RES
<222> LOCATION: (8)..(8)
<223> OTHER INFORMATION: Aminohexanoic acid
<220> FEATURE:
<221> NAME/KEY: MOD_RES
<222> LOCATION: (11)..(11)
<223> OTHER INFORMATION: Beta-alanine

<400> SEQUENCE: 10

Arg Xaa Arg Arg Ala Arg Arg Xaa Arg Arg Ala Arg
```

```
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Aminohexanoic acid
<220> FEATURE:
<221> NAME/KEY: MOD_RES
<222> LOCATION: (6)..(6)
<223> OTHER INFORMATION: Beta-alanine
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (12)..(12)
<223> OTHER INFORMATION: Beta-alanine

<400> SEQUENCE: 11

Cys Arg Xaa Arg Arg Ala Arg Arg Xaa Arg Arg Ala Arg Cys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminohexanoic acid
<220> FEATURE:
<221> NAME/KEY: MOD_RES
<222> LOCATION: (5)..(5)
<223> OTHER INFORMATION: Beta-alanine
<220> FEATURE:
<221> NAME/KEY: MOD_RES
<222> LOCATION: (9)..(9)
<223> OTHER INFORMATION: Aminohexanoic acid
<220> FEATURE:
<221> NAME/KEY: MOD_RES
<222> LOCATION: (12)..(12)
<223> OTHER INFORMATION: Beta-alanine

<400> SEQUENCE: 12

Arg Xaa Arg Arg Ala Arg Cys Arg Xaa Arg Arg Ala Arg Cys
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Gln Ile Lys Ile Trp Phe Cys Asn Lys Arg Ala Lys Ile Lys Lys
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Gln Ile Lys Ile Trp Phe Gln Cys Lys Arg Ala Lys Ile Lys Cys
1               5                   10                  15

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Ser Gln Ile Lys Ile Trp Phe Gln Asn Lys Arg Ala Lys Ile Lys
1               5                   10                  15

Lys Cys

<210> SEQ ID NO 17
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Leu Ile Ile Leu Arg Arg Arg Ile Arg Lys Gln Ala His Ala His
1               5                   10                  15

Ser Lys

<210> SEQ ID NO 18
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Aminohexanoic acid
<220> FEATURE:
<221> NAME/KEY: MOD_RES
<222> LOCATION: (23)..(23)
<223> OTHER INFORMATION: Beta-alanine
<220> FEATURE:
<221> NAME/KEY: MOD_RES
<222> LOCATION: (26)..(26)
<223> OTHER INFORMATION: Aminohexanoic acid
<220> FEATURE:
<221> NAME/KEY: MOD_RES
```

```
<222> LOCATION: (29)..(29)
<223> OTHER INFORMATION: Beta-alanine

<400> SEQUENCE: 18

Leu Leu Ile Ile Leu Arg Arg Arg Ile Arg Lys Gln Ala His Ala His
1               5                   10                  15

Ser Lys Arg Xaa Arg Arg Ala Arg Arg Xaa Arg Arg Ala Arg
            20                  25                  30

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glx Cys Arg Leu Arg Trp Arg Cys
1               5

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Aminohexanoic acid
<220> FEATURE:
<221> NAME/KEY: MOD_RES
<222> LOCATION: (31)..(31)
<223> OTHER INFORMATION: Beta-alanine
<220> FEATURE:
<221> NAME/KEY: MOD_RES
<222> LOCATION: (34)..(34)
<223> OTHER INFORMATION: Aminohexanoic acid
<220> FEATURE:
<221> NAME/KEY: MOD_RES
<222> LOCATION: (37)..(37)
<223> OTHER INFORMATION: Beta-alanine

<400> SEQUENCE: 20

Gly Ile Gly Ala Val Leu Lys Val Leu Thr Thr Gly Leu Pro Ala Leu
1               5                   10                  15

Ile Ser Trp Ile Lys Arg Lys Arg Gln Gln Arg Xaa Arg Arg Ala Arg
            20                  25                  30

Arg Xaa Arg Arg Ala Arg
            35

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Trp Ile Ala Gln Glu Leu Arg Arg Ile Gly Asp Glu Phe Asn Ala
1               5                   10                  15

Tyr Tyr Ala Arg Arg
            20
```

```
<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Arg Ser Ser Arg Ala Gly Leu Gln Trp Pro Val Gly Arg Val His
1               5                   10                  15

Arg Leu Leu Arg Lys
            20

<210> SEQ ID NO 24
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Gly Gly Arg Leu Ser Tyr Ser Arg Arg Arg Phe Ser Thr Ser Thr
1               5                   10                  15

Gly Arg

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Leu Trp Lys Thr Leu Leu Lys Lys Val Leu Lys Ala Pro Lys Lys
1               5                   10                  15
```

Lys Arg Lys Val
            20

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Leu Ser Ser Ile Phe Ser Arg Ile Gly Asp Pro
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Leu Ala Leu Lys Ala Leu Lys Ala Leu Lys Ala Ala Leu Lys Leu
1               5                   10                  15

Ala

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Trp Trp Arg Arg Trp Arg Arg
1               5

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Lys Thr Leu Thr Glu Thr Leu Lys Glu Leu Thr Lys Thr Leu Thr
1               5                   10                  15

Glu Leu

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Arg Leu Pro Pro Pro Val Arg Leu Pro Pro Pro Val Arg Leu Pro
1               5                   10                  15

Pro Pro

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Lys Ile Tyr Asp Lys Lys Val Arg Thr Arg Val Val Lys His
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Gly Thr Tyr Lys Lys Lys Leu Met Arg Ile Pro Leu Lys Gly Thr
1               5                   10                  15

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Tyr Lys Lys Gly Pro Ala Lys Lys Gly Arg Pro Pro Leu Arg Gly
1               5                   10                  15

Trp Phe His

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Ala Trp Val Lys Ala Phe Ile Arg Lys Leu Arg Lys Gly Pro Leu
1               5                   10                  15

Gly

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ser Pro Trp Gly Leu Gln His His Pro Pro Arg Thr
1               5                   10

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Gln Val Thr Ile Trp Ser Gln Asn Arg Arg Val Lys Ser Lys Lys
1               5                   10                  15

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Ser Ala Leu Lys
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Pro Arg Pro Pro Arg Pro Pro Arg
1               5

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Pro Arg Pro Pro Arg Pro Pro Arg Pro Pro Arg
1               5                   10

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Arg Leu Arg Trp Arg
1               5

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Lys Lys Arg Arg Gln Arg Arg Arg
1               5

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Gln Ile Lys Ile Trp Phe Gln Asn Arg Arg Met Lys Trp Lys Lys
1               5                   10                  15

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Arg Arg Arg Arg Arg Arg Arg Arg
1               5

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Val Thr Ile Trp Phe Gln Ser Arg Arg Val Lys Glu Lys Lys
1               5                   10                  15

<210> SEQ ID NO 48
```

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Arg Val Lys Ala Gly Tyr Leu Leu Gly Lys Ile Asn Leu Lys Ala
1               5                   10                  15

Leu Ala Ala Leu Ala Lys Lys Ile Leu
            20                  25

<210> SEQ ID NO 49
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Gly Tyr Leu Leu Gly Lys Ile Asn Leu Lys Ala Leu Ala Ala Leu
1               5                   10                  15

Ala Lys Lys Ile Leu Lys Arg Val Lys
            20                  25

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Arg Val Lys
1

<210> SEQ ID NO 51
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Pro Lys Lys Lys Arg Lys Val Ala Gly Tyr Leu Leu Gly Lys Ile Asn
1               5                   10                  15

Leu Lys Ala Leu Ala Ala Leu Ala Lys Lys Ile Leu
            20                  25

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Gly Tyr Leu Leu Gly Lys Ile Asn Leu Lys Ala Leu Ala Ala Leu
1               5                   10                  15

Ala Lys Lys Ile Leu
            20
```

```
<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Lys Lys Lys Arg Lys Val
1               5

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Asp Gly Thr Leu Ala Val Pro Phe Lys Ala
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Lys Tyr Arg Gly Arg Lys Arg His Pro Arg
1               5                   10

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gctattacct taacccag                                                   18
```

TRIMERIC PEPTIDES FOR ANTISENSE DELIVERY

CROSS REFERENCE TO RELATED APPLICATIONS

This application is a 35 U.S.C. § 371 filing of International Patent Application No. PCT/US2019/043920, filed Jul. 29, 2019, which claims priority to U.S. Provisional Application Ser. No. 62/711,894, file Jul. 30, 2018, which is incorporated herein by reference in its entirety.

SEQUENCE LISTING

The present application is being filed along a Sequence Listing in computer readable format. The Sequence Listing is provided as a file entitled 713921-SPT-012US-SEQ-TXT.txt and is 17.2 bytes in size. The information in the computer readable format of the sequence listing is incorporated herein by reference in its entirety.

BACKGROUND

Antisense technology provides a means for modulating the expression of one or more specific gene products, including alternative splice products, and is uniquely useful in a number of therapeutic, diagnostic, and research applications. The principle behind antisense technology is that an antisense compound, e.g., an oligonucleotide, which hybridizes to a target nucleic acid, modulates gene expression activities such as transcription, splicing, or translation through any one of a number of antisense mechanisms. The sequence specificity of antisense compounds makes them attractive as tools for target validation and gene functionalization, as well as therapeutics to selectively modulate the expression of genes involved in disease.

Although significant progress has been made in the field of antisense technology, there remains a need in the art for oligonucleotides and peptide-oligonucleotide-conjugates having improved antisense or antigene performance.

SUMMARY

Provided herein are trimeric peptide-oligonucleotide-conjugates comprising an oligonucleotide covalently bound to a trimeric peptide. Also provided herein are methods of treating a disease in a subject in need thereof, comprising administering to the subject a trimeric peptide-oligonucleotide-conjugate described herein. Also provided herein is a process for preparing a trimeric peptide-oligonucleotide-conjugates described herein.

Accordingly, in one aspect, provided herein is a trimeric peptide-oligonucleotide conjugate of Formula I:

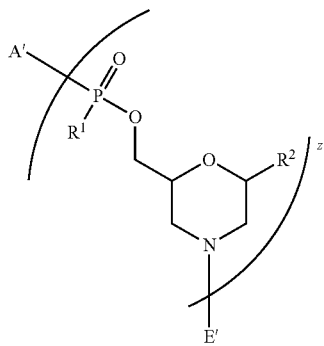

(I)

or a pharmaceutically acceptable salt thereof.

wherein:

A' is selected from —N(H)CH$_2$C(O)NH$_2$, —N(C$_{1-6}$-alkyl)CH$_2$C(O)NH$_2$,

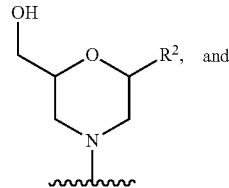

and

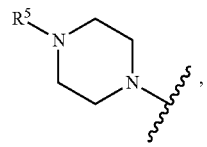

wherein

R$^5$ is —C(O)(O-alkyl)$_x$-OH, wherein x is 3-10 and each alkyl group is, independently at each occurrence, C$_{2-6}$-alkyl, or R$^5$ is selected from —C(O)C$_{1-6}$-alkyl, trityl, monomethoxytrityl, —(C$_{1-6}$-alkyl)-R$^6$, —(C$_{1-6}$-heteroalkyl)-R$^6$, aryl-R$^6$, heteroaryl-R$^6$, —C(O)O—(C$_{1-6}$-alkyl)-R$^6$, —C(O)O-aryl-R$^6$, —C(O)O— heteroaryl-R$^6$, and

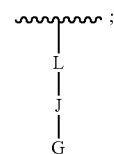

wherein R$^6$ is selected from OH, SH, and NH$_2$, or R$^6$ is O, S, or NH, each of which are covalently-linked to a solid support;

each R$^1$ is independently selected from OH and —N(R$^3$)(R$^4$), wherein each R$^3$ and R$^4$ are, independently at each occurrence, —C$_{1-6}$-alkyl;

each R$^2$ is independently, at each occurrence, selected from H, a nucleobase, and a nucleobase functionalized with a chemical protecting-group, wherein the nucleobase, independently at each occurrence, comprises a C$_{3-6}$-heterocyclic ring selected from pyridine, pyrimidine, triazinane, purine, and deaza-purine;

z is 8-40; and

E' is selected from H, —C$_{1-6}$-alkyl, —C(O)C$_{1-6}$-alkyl, benzoyl, stearoyl, trityl, monomethoxytrityl, dimethoxytrityl, trimethoxytrityl,

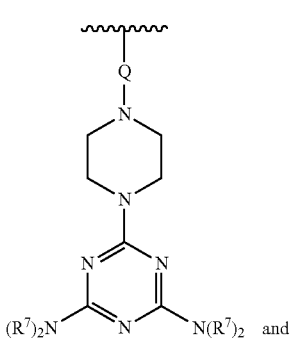

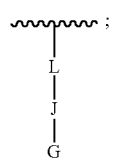

wherein

Q is —C(O)(CH$_2$)$_6$C(O)— or —C(O)(CH$_2$)$_2$S$_2$(CH$_2$)$_2$C(O)—;

R$^7$ is —(CH$_2$)$_2$OC(O)N(R$^8$)$_2$, wherein R$^8$ is —(CH$_2$)$_6$NHC(=NH)NH$_2$;

L is —C(O)(CH$_2$)$_{1-6}$—C$_{7-15}$-heteroaromatic-(CH$_2$)$_{1-6}$C(O)—, wherein L is covalently-linked by an amide bond to the amino-terminus of J;

J is —P$^1$-L$^1$-P$^2$-L$^2$-P$^3$—;

P$^1$, P$^2$, and P$^3$ are each independently a cell-penetrating peptide, wherein P$^1$ and P$^2$ each comprise at least one terminal or internal cysteine residue, and P$^2$ comprises at least one terminal or internal lysine residue;

L$^1$ is

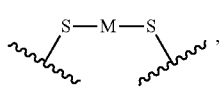

M is

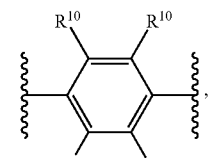

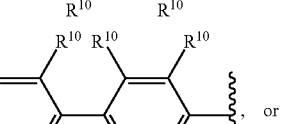

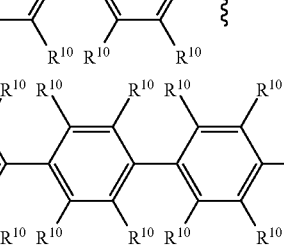

and R$^{10}$ is independently at each occurrence H or a halogen, wherein L$^1$ is covalently-linked to the side chain of a terminal or internal cysteine of P$^1$ and P$^2$;

L$^2$ is —(CH$_2$)$_{1-6}$—C$_{1-6}$-heteroaromatic-(CH$_2$)$_{1-6}$C(O)—, wherein L$^2$ is covalently-linked to the side chain of a terminal or internal lysine on P$^2$ and is covalently-linked by an amide bond to the amino-terminus of P$^3$;

G is selected from H, —C(O)C$_{1-6}$-alkyl, benzoyl, and stearoyl, wherein G is covalently-linked to the carboxy-terminus of J; and wherein at least one of the following conditions is true:

1)

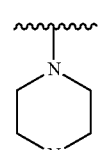

A' is ; or

2)

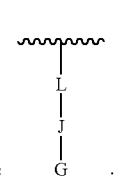

E' is .

In one embodiment, the chimeric peptide-oligonucleotide-conjugate of Formula I is a chimeric peptide-oligonucleotide-conjugate of Formula Ia:

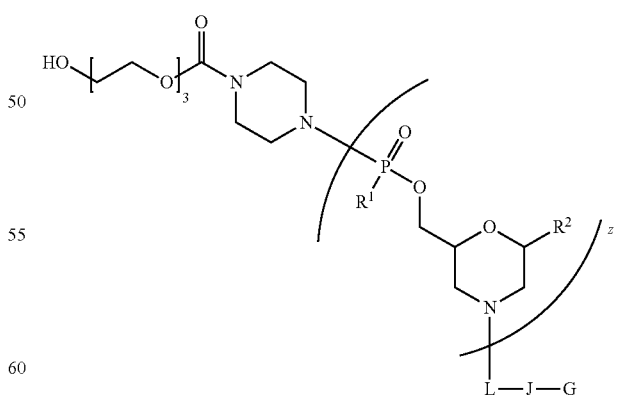

(Ia)

or a pharmaceutically acceptable salt thereof.

In another embodiment, the chimeric peptide-oligonucleotide-conjugate of Formula I is a chimeric peptide-oligonucleotide-conjugate of Formula Ib:

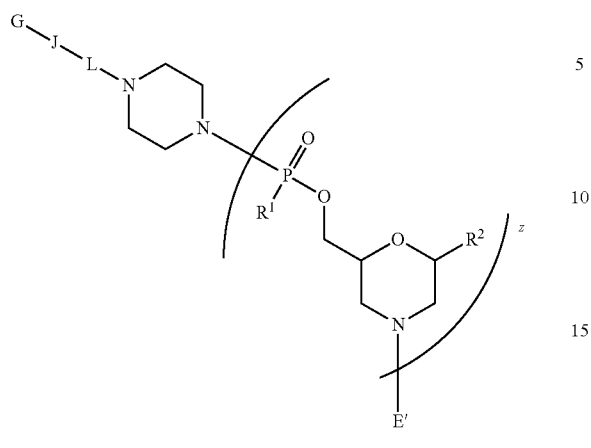

(Ib)

or a pharmaceutically acceptable salt thereof,

In still another aspect, provided herein is a method of treating a neuromuscular disease, comprising administering to the subject a trimeric peptide-oligonucleotide-conjugate of the present disclosure.

In still another aspect, provided herein is A process for preparing a trimeric peptide-oligonucleotide conjugate of Formula (II):

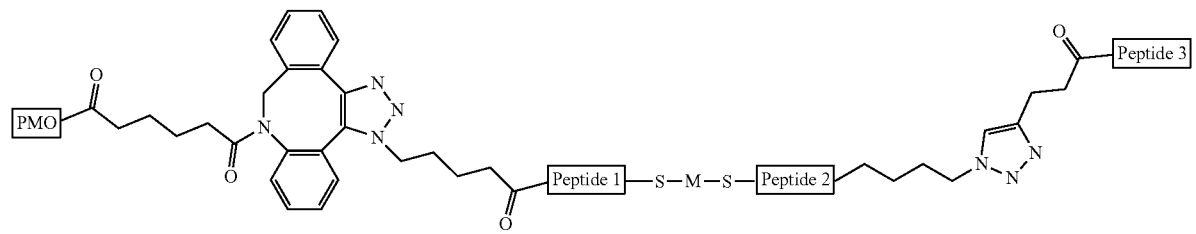

(II)

comprising:
(a) contacting a compound of Formula (III)

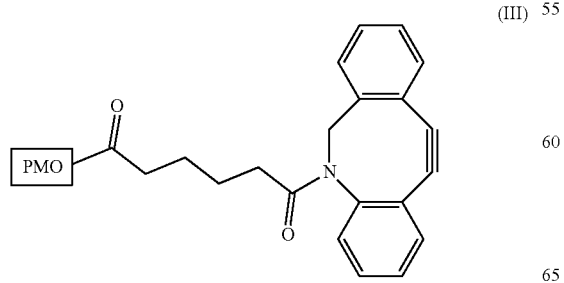

(III)

with a compound of Formula (IV)

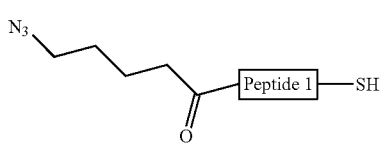

(IV)

in the presence of an acid to form a compound of Formula (V)
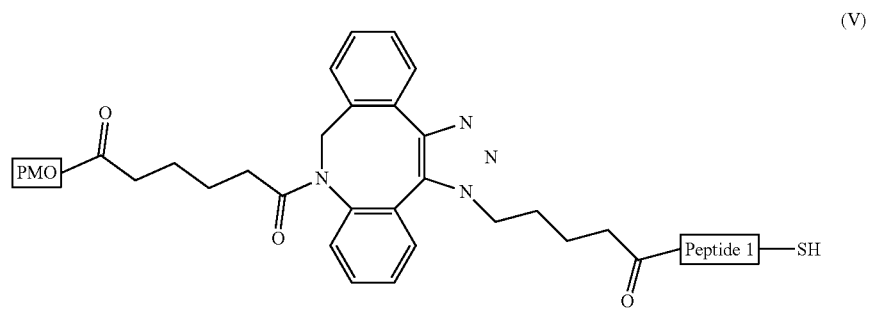
(b) contacting a compound of Formula (VI)
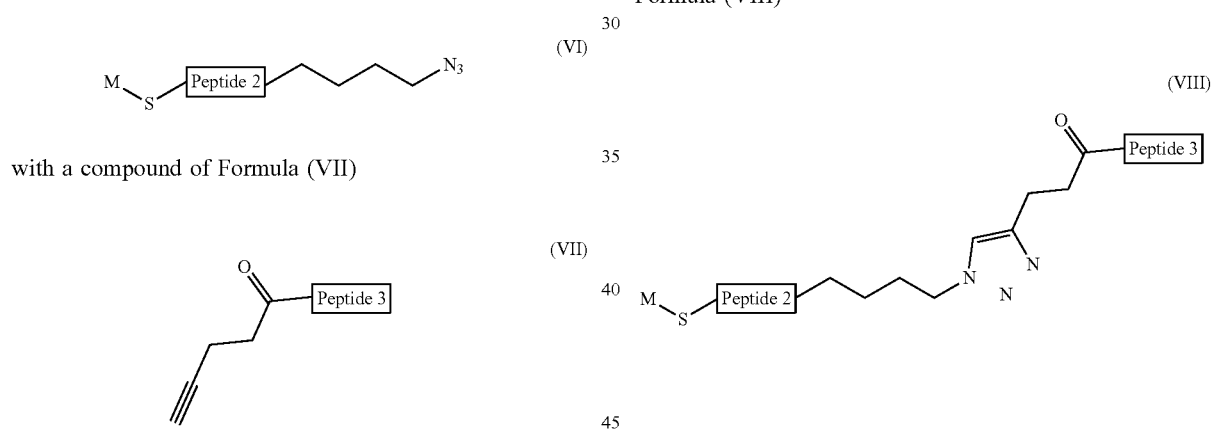
with a compound of Formula (VII)
in the presence of a copper catalyst to form a compound of Formula (VIII)
(c) contacting a compound of Formula (V)
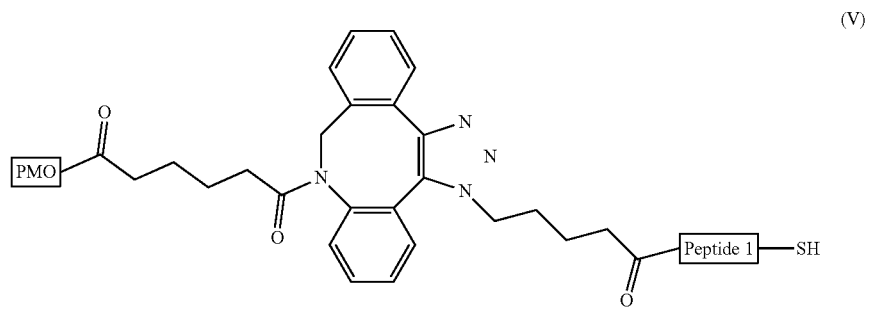

with a compound of Formula (VIII)

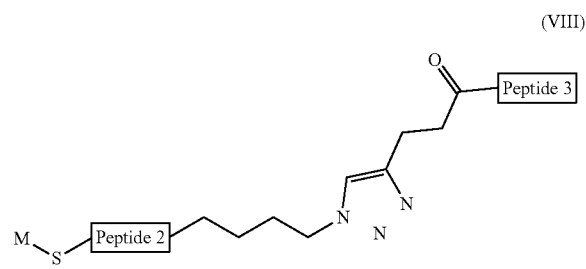

in the presence of a coupling reagent to form a compound of Formula (II).

BRIEF DESCRIPTION OF THE FIGURES

FIG. 3 shows particular peptide sequences and names for the proof-of-concept experiments.

DETAILED DESCRIPTION

Figure 1:
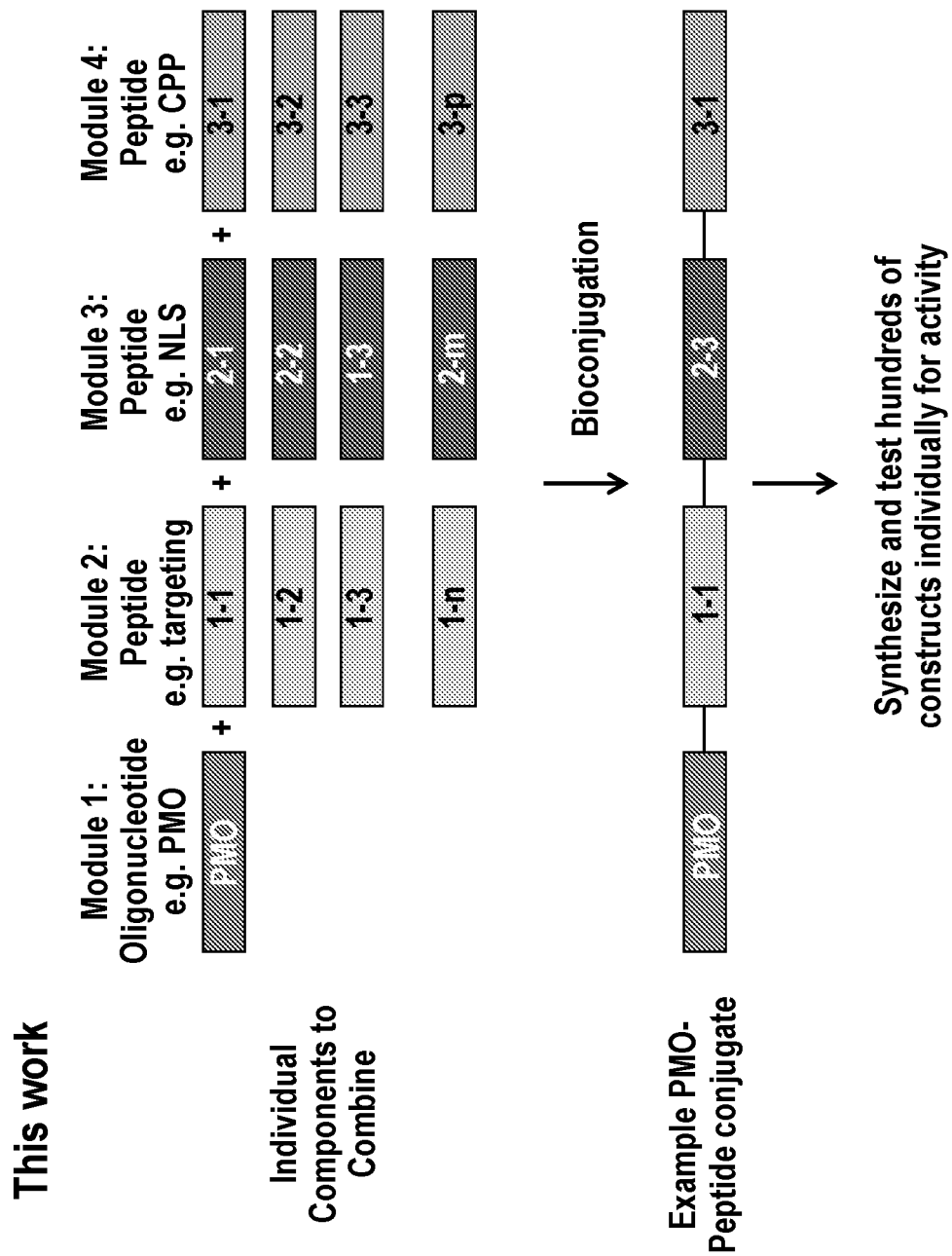
FIG. 1 shows the development and implementation of a four-component modular library. Using bioconjugation, every combination of peptides can be assembled into one construct and tested individually.

Phosphorodiamidate morpholino oligonucleotides (PMOs) are attractive therapeutic molecules for genetic diseases. PMOs are designed to recognize targets by Watson-Crick base pairing and exhibit a high level of specificity for their complimentary nucleotide sequence. Depending on the type of sequence targeted, PMOs can mediate a variety of effects, including blocking protein translation or modifying gene splicing. Eteplirsen, a PMO approved by the FDA to treat Duchenne muscular dystrophy, causes a mutation-containing exon in the pre-mRNA encoding for dystrophin to be excluded from the final protein transcript, restoring protein functionality.

In terms of structure, PMOs are neutral oligonucleotide analogues in which the ribosyl ring has been replaced with a morpholino ring and the negatively-charged phosphodiester backbone has been replaced with the uncharged phosphorodiamidate. The altered backbone structure prevents degradation in both serum and by intracellular nucleases. However, the relatively large size and neutral charge of PMOs can lead to inefficient delivery to the cytosol and nucleus.

Cell-penetrating peptides (CPPs) are a promising strategy to improve the delivery of PMO to the nucleus. CPPs are relatively short sequences of 5-40 amino acids that ideally access the cytosol and can promote the intracellular delivery of cargo. CPPs can be classified into different groups based on their physicochemical properties. One common CPP class consists of repetitive, arginine-based peptides such as $R_{12}$ and Bpep (RXRRβRRXRRβR, in which X is aminohexanoic acid and β is β-alanine). These oligoarginine peptides are often random coils. When conjugated to PMO, the oligoarginine peptides have been some of the most effective peptides in promoting PMO delivery. Other CPPs, such as Penetratin, pVEC, and melittin, are more amphipathic in nature. While these sequences do contain cationic residues, the defined separation of charged and hydrophobic residues can promote amphipathic helix formation. However, amphipathic CPPs have not been demonstrated to significantly improve PMO efficacy.

No universal mechanism of cell entry exists for CPPs or CPP-PMO conjugates. The mechanism is often highly dependent on the treatment concentrations and the type of cargo attached. Above a certain threshold concentration (generally low micromolar), energy-independent cytosolic uptake can be observed faster than the time scale of endocytosis and cell surface recycling. The fast uptake rate provides evidence for a direct translocation mechanism similar to what is observed for a small molecule. However, at low, physiologically-relevant concentrations, uptake is primarily endocytic. Even within the category of endocytosis, CPPs and CPP-PMO conjugates can enter cells using one or multiple endocytic mechanisms. These endocytic mechanisms include micropinocytosis, clathrin-mediated endocytosis, caveolae-mediated endocytosis and clathrin/caveloae-independent endocytosis. CPP-PMO conjugates are primarily endocytosed at low concentrations, and the CPPs that are poor for PMO delivery are likely trapped in endosomes or excluded from the nuclear compartment.

Provided herein are trimeric peptide-PMO conjugates for improving PMO delivery. These trimeric peptide-PMO conjugates are comprised of three or more CPPs covalently linked to one another and conjugated with PMOs. An increase in cellular uptake of the oligonucleotide, especially when compared to unconjugated PMOs and single CPP-PMO conjugates, is described herein.

Definitions

Listed below are definitions of various terms used to describe this disclosure. These definitions apply to the terms as they are used throughout this specification and claims, unless otherwise limited in specific instances, either individually or as part of a larger group.

The term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, 1%, and ±0.1% from the specified value, as such variations are appropriate to perform the disclosed methods.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$—CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

The term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. In various embodiments, examples of an aryl group may include phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_{6-12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_{1-9}$-heteroaryl indicates the number of carbon atoms contained in the heteroaryl group without including the number of heteroatoms. For example, a $C_{1-9}$-heteroaryl will include an additional one to four heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the acronym DBCO refers to 8,9-dihydro-3H-dibenzo[b,f][1,2,3]triazolo[4,5-d]azocine.

The term "protecting group" or "chemical protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, monomethoxytrityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while coexisting amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

The term "nucleobase," "base pairing moiety," "nucleobase-pairing moiety," or "base" refers to the heterocyclic ring portion of a nucleoside, nucleotide, and/or morpholino subunit. Nucleobases may be naturally occurring, or may be modified or analogs of these naturally occurring nucleobases, e.g., one or more nitrogen atoms of the nucleobase may be independently at each occurrence replaced by carbon. Exemplary analogs include hypoxanthine (the base component of the nucleoside inosine); 2,6-diaminopurine;

5-methyl cytosine; C5-propynyl-modified pyrimidines; 10-(9-(aminoethoxy)phenoxazinyl) (G-clamp) and the like.

Further examples of base pairing moieties include, but are not limited to, uracil, thymine, adenine, cytosine, guanine and hypoxanthine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, RNA, 2003, 9, 1034-1048, Limbach et al. Nucleic Acids Research, 1994, 22, 2183-2196 and Revankar and Rao, Comprehensive Natural Products Chemistry, vol. 7, 313, are also contemplated, the contents of which are incorporated herein by reference.

Further examples of base pairing moieties include, but are not limited to, expanded-size nucleobases in which one or more benzene rings has been added. Nucleic base replacements described in the Glen Research catalog (www.glen-research.com); Krueger A T et al., Acc. Chem. Res., 2007, 40, 141-150; Kool, ET, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, the contents of which are incorporated herein by reference, are contemplated as useful for the synthesis of the oligomers described herein. Examples of expanded-size nucleobases are shown below:

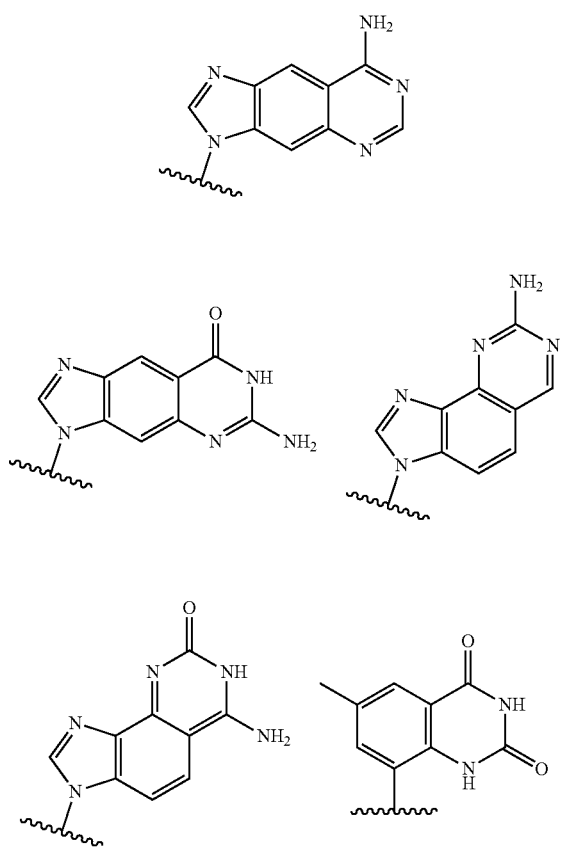

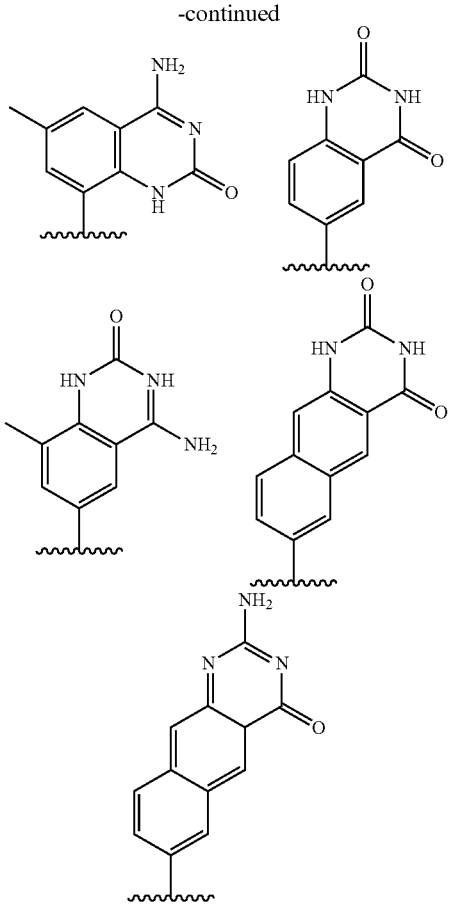

The terms "oligonucleotide" or "oligomer" refer to a compound comprising a plurality of linked nucleosides, nucleotides, or a combination of both nucleosides and nucleotides. In specific embodiments provided herein, an oligonucleotide is a morpholino oligonucleotide.

The phrase "morpholino oligonucleotide" or "PMO" refers to a modified oligonucleotide having morpholino subunits linked together by phosphoramidate or phosphorodiamidate linkages, joining the morpholino nitrogen of one subunit to the 5'-exocyclic carbon of an adjacent subunit. Each morpholino subunit comprises a nucleobase-pairing moiety effective to bind, by nucleobase-specific hydrogen bonding, to a nucleobase in a target.

The terms "antisense oligomer," "antisense compound" and "antisense oligonucleotide" are used interchangeably and refer to a sequence of subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The oligomer may have exact (perfect) or near (sufficient) sequence complementarity to the target sequence; variations in sequence near the termini of an oligomer are generally preferable to variations in the interior.

Such an antisense oligomer can be designed to block or inhibit translation of mRNA or to inhibit/alter natural or abnormal pre-mRNA splice processing, and may be said to be "directed to" or "targeted against" a target sequence with which it hybridizes. The target sequence is typically a region including an AUG start codon of an mRNA, a Translation Suppressing Oligomer, or splice site of a pre-processed mRNA, a Splice Suppressing Oligomer (SSO). The target sequence for a splice site may include an mRNA sequence having its 5' end 1 to about 25 base pairs downstream of a normal splice acceptor junction in a preprocessed mRNA. In various embodiments, a target sequence may be any region of a preprocessed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

The antisense oligonucleotide and the target RNA are complementary to each other when a sufficient number of corresponding positions in each molecule are occupied by nucleotides which can hydrogen bond with each other, such that stable and specific binding occurs between the oligonucleotide and the target. Thus, "specifically hybridizable" and "complementary" are terms which are used to indicate a sufficient degree of complementarity or precise pairing such that stable and specific binding occurs between the oligonucleotide and the target. It is understood in the art that the sequence of an oligonucleotide need not be 100% complementary to that of its target sequence to be specifically hybridizable. An oligonucleotide is specifically hybridizable when binding of the oligonucleotide to the target molecule interferes with the normal function of the target RNA, and there is a sufficient degree of complementarity to avoid non-specific binding of the antisense oligonucleotide to non-target sequences under conditions in which specific binding is desired, i.e., under physiological conditions in the case of in vivo assays or therapeutic treatment, and in the case of in vitro assays, under conditions in which the assays are performed.

Oligonucleotides may also include nucleobase (often referred to in the art simply as "base") modifications or substitutions. Oligonucleotides containing a modified or substituted base include oligonucleotides in which one or more purine or pyrimidine bases most commonly found in nucleic acids are replaced with less common or non-natural bases. In some embodiments, the nucleobase is covalently linked at the N9 atom of the purine base, or at the N1 atom of the pyrimidine base, to the morpholine ring of a nucleotide or nucleoside.

Purine bases comprise a pyrimidine ring fused to an imidazole ring, as described by the general formula:

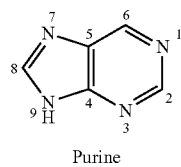

Purine

Adenine and guanine are the two purine nucleobases most commonly found in nucleic acids. These may be substituted with other naturally-occurring purines, including but not limited to N6-methyladenine, N2-methylguanine, hypoxanthine, and 7-methylguanine.

Pyrimidine bases comprise a six-membered pyrimidine ring as described by the general formula:

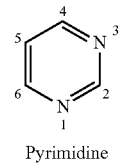

Pyrimidine

Cytosine, uracil, and thymine are the pyrimidine bases most commonly found in nucleic acids. These may be substituted with other naturally-occurring pyrimidines, including but not limited to 5-methylcytosine, 5-hydroxymethylcytosine, pseudouracil, and 4-thiouracil. In one embodiment, the oligonucleotides described herein contain thymine bases in place of uracil.

Other modified or substituted bases include, but are not limited to, 2,6-diaminopurine, orotic acid, agmatidine, lysidine, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; N2-cyclopentylguanine (cPent-G), N2-cyclopentyl-2-aminopurine (cPent-AP), and N2-propyl-2-aminopurine (Pr-AP), pseudouracil or derivatives thereof; and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Pseudouracil is a naturally occurring isomerized version of uracil, with a C-glycoside rather than the regular N-glycoside as in uridine.

Certain modified or substituted nucleobases are particularly useful for increasing the binding affinity of the antisense oligonucleotides of the disclosure. These include 5-substituted pyrimidines, 6-azapyrimidines and N-2, N-6 and 0-6 substituted purines, including 2-aminopropyladenine, 5-propynyluracil and 5-propynylcytosine. In various embodiments, nucleobases may include 5-methylcytosine substitutions, which have been shown to increase nucleic acid duplex stability by 0.6-1.2° C.

In some embodiments, modified or substituted nucleobases are useful for facilitating purification of antisense oligonucleotides. For example, in certain embodiments, antisense oligonucleotides may contain three or more (e.g., 3, 4, 5, 6 or more) consecutive guanine bases. In certain antisense oligonucleotides, a string of three or more consecutive guanine bases can result in aggregation of the oligonucleotides, complicating purification. In such antisense oligonucleotides, one or more of the consecutive guanines can be substituted with hypoxanthine. The substitution of hypoxanthine for one or more guanines in a string of three or more consecutive guanine bases can reduce aggregation of the antisense oligonucleotide, thereby facilitating purification.

The oligonucleotides provided herein are synthesized and do not include antisense compositions of biological origin. The molecules of the disclosure may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution, or absorption, or a combination thereof.

The terms "complementary" and "complementarity" refer to oligonucleotides (i.e., a sequence of nucleotides) related by base-pairing rules. For example, the sequence "T-G-A (5'-3')," is complementary to the sequence "T-C-A (5'-3')." Complementarity may be "partial," in which only some of the nucleic acids' bases are matched according to base pairing rules. Or, there may be "complete," "total," or "perfect" (100%) complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Such hybridization may occur with "near" or "substantial" complementarity of the antisense oligomer to the target sequence, as well as with exact complementarity. In some embodiments, an oligomer may hybridize to a target sequence at about 50%, 55%, 60%, 65%, 70%, 75%, 80%, 85%, 90%, 95%, 99% or 100% complementarity. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5-terminus, 3'-terminus, or both termini.

The term "peptide" refers to a compound comprising a plurality of linked amino acids. The peptides provided herein can be considered to be cell penetrating peptides.

The terms "cell penetrating peptide" and "CPP" are used interchangeably and refer to cationic cell penetrating peptides, also called transport peptides, carrier peptides, or peptide transduction domains. The peptides, provided herein, have the capability of inducing cell penetration within 100% of cells of a given cell culture population and allow macromolecular translocation within multiple tissues in vivo upon systemic administration. In various embodiments, a CPP embodiment of the disclosure may include an arginine-rich peptide as described further below.

As used herein, the term "chimeric peptide" refers to a polypeptide that comprises a first portion that is a first peptide or a fragment thereof, fused to a second portion that is a different peptide or fragment thereof. The chimeric peptide can comprise 2 or more covalently linked peptides. The peptides may be covalently linked via the amino acid side chain, the N-terminus, the C-terminus, or any combination thereof. In certain embodiments, the peptides are covalently linked via the N-terminus of one peptide to the C-terminus of the other. In certain embodiments, the covalent linker is an amide bond.

As used herein, the term "trimeric peptide" refers to a polypeptide that comprises a first portion that is a first peptide or a fragment thereof, fused to a second portion that is a different peptide or fragment thereof, fused to a third portion that is a different peptide or fragment thereof. The trimeric peptide can comprise 3 or more covalently linked peptides. The peptides may be covalently linked via the amino acid side chain, the N-terminus, the C-terminus, or any combination thereof. In certain embodiments, the peptides are covalently linked via the N-terminus of one peptide to the C-terminus of the other. In certain embodiments, the covalent linker is an amide bond.

As used herein, the term "amphipathic peptide" refers to a peptide with separated regions of essentially charged amino acids and essentially uncharged amino acids. These regions are known as the hydrophilic peptidyl segment and the hydrophobic peptidyl segment, respectively.

As used herein, the term "oligoarginine peptide" refers to a peptide where the peptide is comprised of all arginine or mostly arginine amino acid residues. In certain embodiments, the peptide is comprised entirely of arginine amino acid residues. In certain embodiments, the peptide is comprised of 50-99% arginine amino acid residues interspaced with amino acid linkers, such as, but not limited to, aminohexanoic acid or beta-alanine. In certain embodiments, the peptide is comprised of 75% arginine amino acid residues interspaced with amino acid linkers, such as, but not limited to, aminohexanoic acid or beta-alanine.

As used herein, the term "nuclear targeting peptide" refers to a peptide where the peptide contains a nuclear localization sequence that allows for the protein to import into the cell nucleus by nuclear transport. In a certain embodiment, this sequence consists of one or more positively charged amino acids exposed on the protein surface.

As used herein, the term "endosomal disrupting peptide" refers to a peptide where the peptide may help release of agents into the cytoplasm of cells. In a certain embodiment, this sequence consists of one or more positively charged amino acids.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect.

The term "amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

As used herein, "pharmaceutically acceptable salts" refers to derivatives of the disclosed oligonucleotides wherein the parent oligonucleotide is modified by converting an existing acid or base moiety to its salt form. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Trimeric Peptide-Oligonucleotide-Conjugates

Provided herein are oligonucleotides chemically linked to a trimeric cell-penetrating peptide. The trimeric cell-penetrating peptide enhances activity, cellular distribution, or cellular uptake of the oligonucleotide. In particular, the trimeric cell-penetrating peptide comprises an amphipathic peptide, a nuclear targeting peptide, an endosomal disrupting peptide, a chimeric peptide, a cyclic peptide, a bicyclic peptide, an oligoarginine peptide, or any combination thereof.

The oligonucleotides can additionally be chemically-linked to one or more heteroalkyl moieties (e.g., polyethylene glycol) that further enhance the activity, cellular distribution, or cellular uptake of the oligonucleotide. In one exemplary embodiment, the trimeric cell-penetrating peptide is covalently coupled at its N-terminal or C-terminal residue to either end, or both ends, of the oligonucleotide.

Thus, in one aspect, provided herein is a trimeric peptide-oligonucleotide conjugate of Formula I:

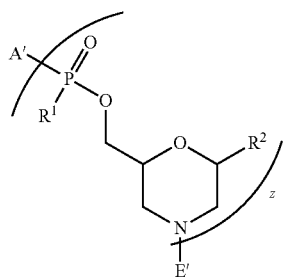
(I)

or a pharmaceutically acceptable salt thereof, wherein:
A' is selected from —N(H)CH$_2$C(O)NH$_2$, —N(C$_{1-6}$-alkyl)CH$_2$C(O)NH$_2$,

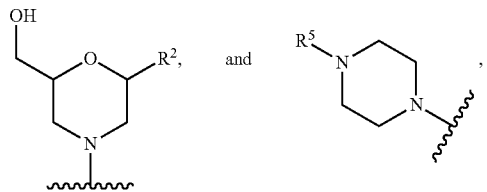

wherein
R$^5$ is —C(O)(O-alkyl)$_x$-OH, wherein x is 3-10 and each alkyl group is, independently at each occurrence, C$_{2-6}$-alkyl,
or R$^5$ is selected from —C(O)C$_{1-6}$-alkyl, trityl, monomethoxytrityl, —(C$_{1-6}$-alkyl)-R$^6$, —(C$_{1-6}$-heteroalkyl)-R$^6$, aryl-R$^6$, heteroaryl-R$^6$, —C(O)O—(C$_{1-6}$-alkyl)-R$^6$, —C(O)O-aryl-R$^6$, —C(O)O— heteroaryl-R$^6$, and

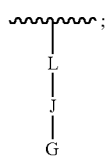

wherein R$^6$ is selected from OH, SH, and NH$_2$, or R$^6$ is O, S, or NH, each of which are covalently-linked to a solid support;
each R$^1$ is independently selected from OH and —N(R$^3$)(R$^4$), wherein each R$^3$ and R$^4$ are, independently at each occurrence, —C$_{1-6}$-alkyl;

each R$^2$ is independently, at each occurrence, selected from H, a nucleobase, and a nucleobase functionalized with a chemical protecting-group, wherein the nucleobase, independently at each occurrence, comprises a C$_{3-6}$-heterocyclic ring selected from pyridine, pyrimidine, triazinane, purine, and deaza-purine;
z is 8-40; and
E' is selected from H, —C$_{1-6}$-alkyl, —C(O)C$_{1-6}$-alkyl, benzoyl, stearoyl, trityl, monomethoxytrityl, dimethoxytrityl, trimethoxytrityl,

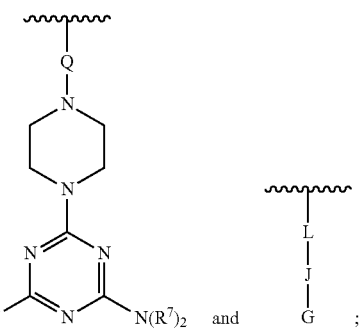

wherein
Q is —C(O)(CH$_2$)$_6$C(O)— or —C(O)(CH$_2$)$_2$S$_2$(CH$_2$)$_2$C(O)—;
R$^7$ is —(CH$_2$)$_2$OC(O)N(R$^8$)$_2$, wherein R$^8$ is —(CH$_2$)$_6$NHC(=NH)NH$_2$;
P$^1$, P$^2$, and P$^3$ are each independently a cell-penetrating peptide, wherein P1 and P2 each comprise at least one cysteine amino acid residue, and P$^2$ comprises at least one lysine;
J is —P$^1$-L$^1$-P$^2$-L$^2$-P$^3$—;
P$^1$, P$^2$, and P$^3$ are each independently a cell-penetrating peptide, wherein P$^1$ and P$^2$ each comprise at least one terminal or internal cysteine residue, and P$^2$ comprises at least one terminal or internal lysine residue;

L$^1$ is 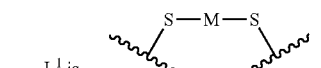,

M is 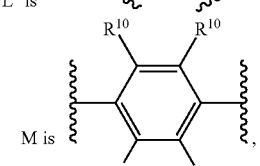,

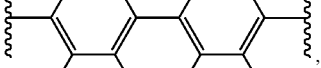, or
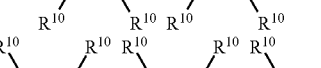
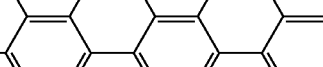
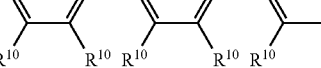, and R$^{10}$ is independently at each occurrence H or a halogen, wherein $L^1$ is covalently-linked to the side chain of a terminal or internal cysteine of $P^1$ and $P^2$;

$L^2$ is —$(CH_2)_{1-6}$—$C_{1-6}$-heteroaromatic-$(CH_2)_{1-6}C(O)$—, wherein $L^2$ is covalently-linked to the side chain of a terminal or internal lysine on $P^2$ and is covalently-linked by an amide bond to the amino-terminus of $P^3$;

G is selected from H, —$C(O)C_{1-6}$-alkyl, benzoyl, and stearoyl, wherein G is covalently-linked to the carboxy-terminus of J; and wherein at least one of the following conditions is true:

1)

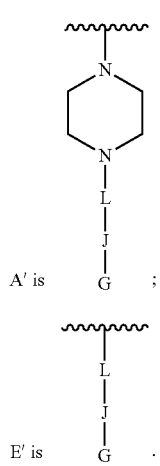

A' is

2)

E' is

In an embodiment, when $P^1$ and $P^2$ each comprise at least one cysteine amino acid residue, wherein the cysteine amino acid residue replaced one of the original amino acid residues.

In another embodiment, when $P^1$ and $P^2$ each comprise at least one cysteine amino acid residue, wherein the cysteine amino acid residue is an additional residue to the original amino acid residues.

In an embodiment, $P^2$ comprises at least one lysine amino acid residue, wherein the lysine amino acid residue replaced one of the original amino acid residues.

In another embodiment, $P^2$ comprises at least one lysine amino acid residue, wherein the lysine amino acid residue is an additional residue to the original amino acid residues.

In one embodiment, z is 8-30. In another embodiment, z is 10-30. In a further embodiment, z is 15-25. In another embodiment, z is 20-25. In an embodiment, z is 8, 9, 10, 11, 12, 13, 14, 15, 16, 17, 18, 19, 20, 21, 22, 23, 24, 25, 26, 27, 28, 29, or 30.

In yet another embodiment, E' is selected from H, —$C_{1-6}$-alkyl, —$C(O)C_{1-6}$-alkyl, benzoyl, stearoyl, trityl, monomethoxytrityl, dimethoxytrityl, trimethoxytrityl, and

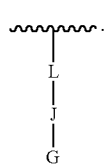

In another embodiment, A' is selected from —$N(C_{1-6}$-alkyl)$CH_2C(O)NH_2$,

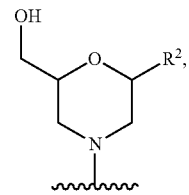

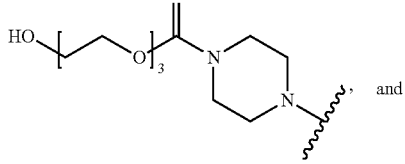, and

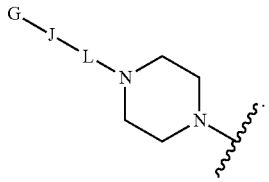.

In still another embodiment, E' is selected from H, —$C(O)CH_3$, benzoyl, stearoyl, trityl, 4-methoxytrityl, and

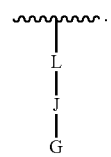.

In yet another embodiment, A' is selected from —$N(C_{1-6}$-alkyl)$CH_2C(O)NH_2$,

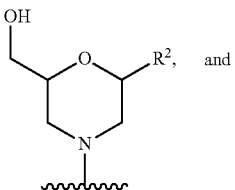

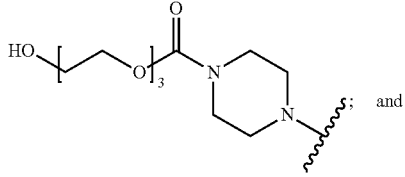; and

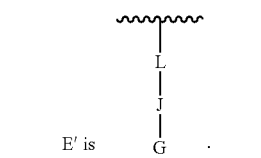.

E' is 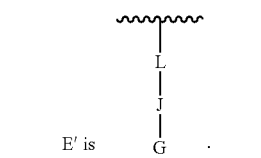.

In another embodiment, A' is

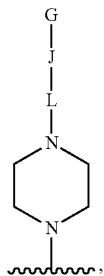

and

E' is selected from H, —C(O)CH$_3$, trityl, 4-methoxytrityl, benzoyl, and stearoyl.

In an embodiment, the trimeric peptide-oligonucleotide conjugate of Formula I is a chimeric peptide-oligonucleotide conjugate of Formula Ia:

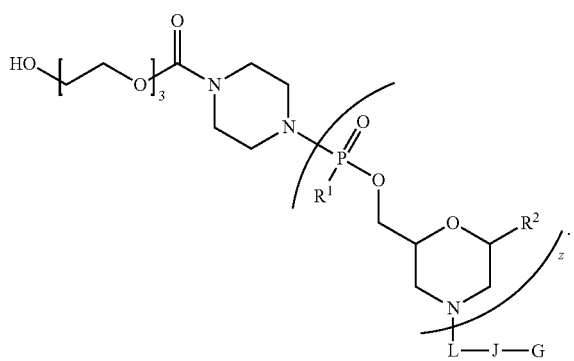

(Ia)

In an embodiment, the chimeric peptide-oligonucleotide conjugate of Formula I is a chimeric peptide-oligonucleotide conjugate of Formula Ib:

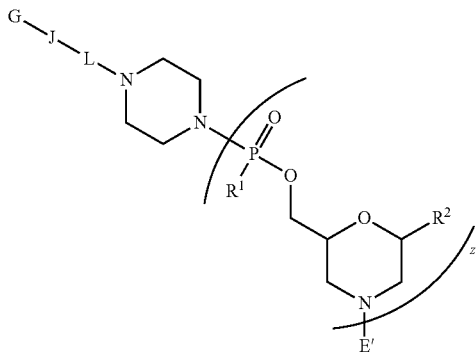

(Ib)

wherein E' is selected from H, C$_{1-6}$-alkyl, —C(O)CH$_3$, benzoyl, and stearoyl.

In an embodiment, each of the cell-penetrating peptides are independently an amphipathic peptide, a nuclear targeting peptide, an endosomal disrupting peptide, a chimeric peptide, a cyclic peptide, a bicyclic peptide, or an oligoarginine peptide.

In another embodiment, P$^1$ is an amphipathic peptide.

In yet another embodiment, P$^2$ is a nuclear targeting peptide.

In still another embodiment, the amphipathic peptide comprises a hydrophobic peptidyl segment and a hydrophilic peptidyl segment, wherein the hydrophobic peptidyl segment comprises a sequence of 2 to 10 amino acids independently selected from glycine, isoleucine, alanine, valine, leucine, phenylalanine, tyrosine, or tryptophan, and wherein the hydrophilic peptidyl segment comprises a sequence of 2-20 amino acids independently selected from charged amino acids, uncharged but polar amino acids, or hydrophobic amino acids, wherein the hydrophilic peptidyl segment comprises at least one non-hydrophobic amino acid.

In an embodiment, the hydrophophilic peptidyl segment comprises a sequence of 2 to 20 amino acids independently selected from arginine, lysine, glutamine, asparagine, histidine, serine, threonine, tryptophan, alanine, isoleucine, leucine, methionine, phenylalanine, valine, proline, or glycine, wherein the hydrophilic peptidyl segment comprises at least one non-hydrophobic amino acid.

In another embodiment, P$^1$ is Penetratin, pVEC, TP10, or DPV6.

In yet another embodiment, P$^2$ is KRVK, SV40, or AAV-PHP.eB.

In a further embodiment, P$^3$ is DPV6, PPC3, PPC5, R12, R12 full cycle, R12 N-cycle, R12 C-cycle, R12 benzyl bicycle, R12 double cycle, Bpep, Bpep full cycle, Bpep C-cycle, Penetratin (nle), Engrailed N-cycle, Engrailed C-cycle, Engrailed full cycle, pVEC, pVEC-Bpep, AIP6 full cycle, Melittin-Bpep, Bh3 helix, Bac7, Buforin 2, Melittin, SynB1, S413-PVrev, Ribotoxin2 L3, PreS2-TLM, MAP, W/R, MAP12, SAP, SVM1, SVM3, SVM4, YTA4, 439a, HoxA13 serine2, Bip, PPR3, PPR4, AIP6, DPV15b, TAT, Penetratin, R9, HoxA13 serine1, KRVK TP10, TP10 KRVK, or SV40 TP10.

In an embodiment, P$^1$ is DPV6.

In another embodiment, P$^3$ is DPV6, Bpep, pVEC-Bpep, Buforin 2, SynB1, W/R, or AIP6.

In yet another embodiment, P$^1$ is DPV6, P$^2$ is SV40, and P$^3$ is DPV6, Bpep, pVEC-Bpep, Buforin 2, SynB1, W/R, or AIP6.

In a further embodiment, P$^1$ is DPV6, P$^2$ is SV40, and P$^3$ is pVEC-Bpep.

In an embodiment, P$^1$ is DPV6, P$^2$ is SV40, and P$^3$ is W/R.

In another embodiment, P$^1$ is DPV6, P$^2$ is SV40, and P$^3$ is SynB1.

In an embodiment of Formula I, Ia, and Ib, each R$^1$ is N(CH$_3$)$_2$.

In yet another embodiment of Formula I, Ia, and Ib, each R$^2$ is a nucleobase, wherein the nucleobase independently at each occurrence comprises a C$_{4-6}$-heterocyclic ring selected from pyridine, pyrimidine, triazinane, purine, and deazapurine.

In another embodiment of Formula I, Ia, and Ib, each R² is a nucleobase, wherein the nucleobase independently at each occurrence comprises a $C_{4-6}$-heterocyclic ring selected from pyrimidine, purine, and deaza-purine.

In still another embodiment of Formula I, Ia, and Ib, each R² is a nucleobase independently at each occurrence selected from adenine, 2,6-diaminopurine, 7-deazaadenine, guanine, 7-deaza-guanine, hypoxanthine, cytosine, 5-methyl-cytosine, thymine, uracil, and hypoxanthine.

In yet another embodiment of Formula I, Ia, and Ib, each R² is a nucleobase independently at each occurrence selected from adenine, guanine, cytosine, 5-methyl-cytosine, thymine, uracil, and hypoxanthine.

In another embodiment of Formula I, Ia, and Ib, L is —C(O)(CH₂)₁₋₆-DBCO-(CH₂)₁₋₆C(O)—.

In another embodiment of Formula I, Ia, and Ib, L is

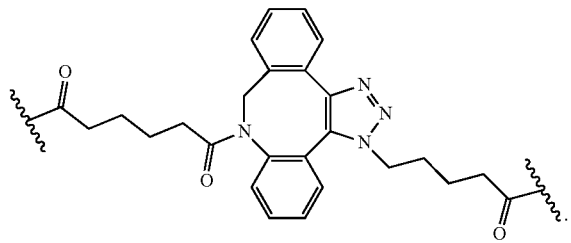 [SMILES: *C(=O)CCCCC(=O)N1Cc2ccccc2-c2nnn(CCCCC(*)=O)c2-c2ccccc21]

In another embodiment of Formula I, Ia, and Ib, M is

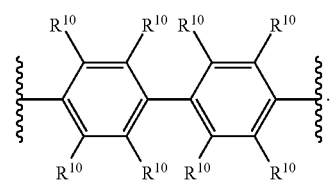

In yet another embodiment of Formula I, Ia, and Ib, M is

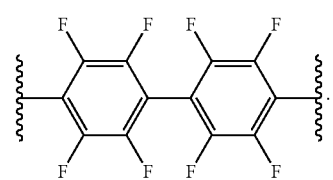 [SMILES: *c1c(F)c(F)c(-c2c(F)c(F)c(*)c(F)c2F)c(F)c1F]

In another embodiment of Formula I, Ia, and Ib, L¹ is covalently-linked to the side chain of a terminal cysteine on P¹ and P² to form the structure:

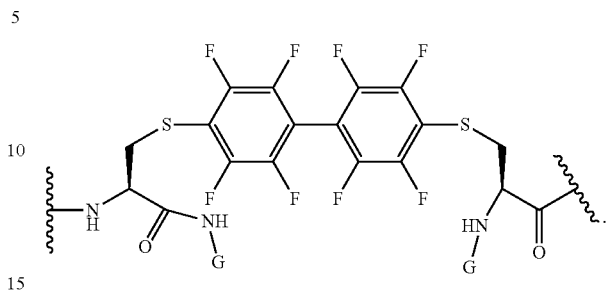

In another embodiment of Formula I, Ia, and Ib, L² is covalently-linked to the side chain of a terminal lysine on P² and is covalently-linked by an amide bond to the amino-terminus of P³ to form the structure:

In another embodiment of Formula I, Ia, and Ib, G is selected from H, C(O)CH₃, benzoyl, and stearoyl.

In still another embodiment of Formula I, Ia, and Ib, G is H or —C(O)CH₃.

In yet another embodiment of Formula I, Ia, and Ib, G is H.

In yet another embodiment of Formula I, Ia, and Ib, G is —C(O)CH₃.

In yet another embodiment of Formula I, Ia, and Ib, the trimeric oligonucleotide-peptide conjugate demonstrates at least a 20-fold improvement in uptake as compared to unconjugated oligonucleotide.

In an embodiment, the trimeric oligonucleotide-peptide conjugate demonstrates at least a three-fold improvement in uptake as compared to non-trimeric oligonucleotide-peptide conjugates.

In another embodiment, the trimeric oligonucleotide-peptide conjugate demonstrates improvement in uptake as compared to the corresponding non-trimeric penetratin-peptide conjugate.

Representative peptide-oligonucleotide-conjugates of the disclosure include, amongst others, trimeric peptide-oligonucleotide-conjugates of the following structure:

(IV)

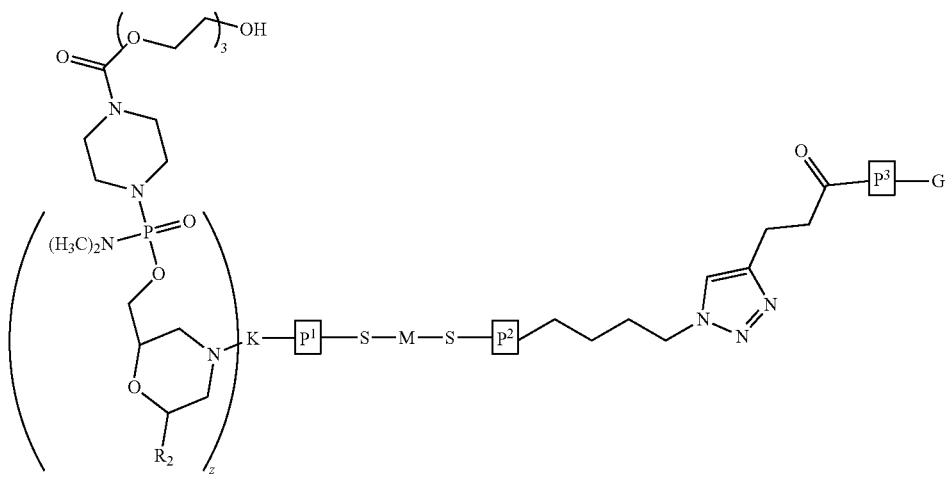

or a pharmaceutically acceptable salt thereof, wherein

G is H or —C(O)CH$_3$;

R$^2$ is a nucleobase, independently at each occurrence, selected from adenine, guanine, cytosine, 5-methylcytosine, thymine, uracil, and hypoxanthine;

K is —C(O)(CH$_2$)$_{1-6}$—C$_{7-15}$-heteroaromatic-(CH$_2$)$_{1-6}$C(O)—;

M is

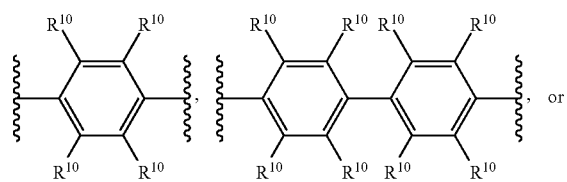, or

-continued

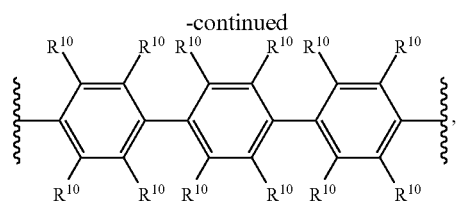

and R$^{10}$ is independently at each occurrence H or a halogen, wherein L$^1$ is covalently-linked to the side chain of a terminal or internal cysteine on P$^1$ and P$^2$ z is 8-40; and P$^1$, P$^2$, and P$^3$ are each independently a cell-penetrating peptide, wherein P$^1$ and P$^2$ each comprise at least one cysteine amino acid residue, and wherein each of the cell-penetrating peptides are independently an amphipathic peptide, a nuclear targeting peptide, an endosomal disrupting peptide, a chimeric peptide, a cyclic peptide, a bicyclic peptide, or an oligoarginine peptide.

In an embodiment, the structure of Formula (IV) is Formula (IVa):

(IVa)

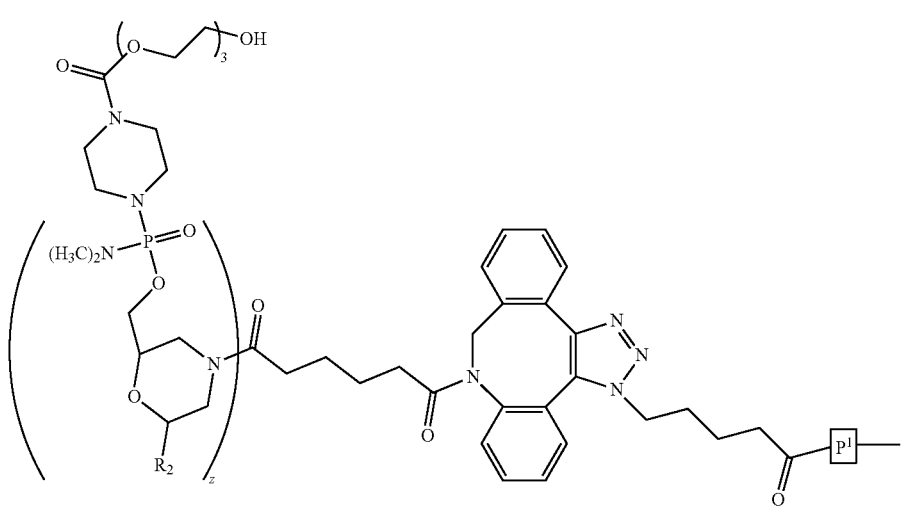

-continued

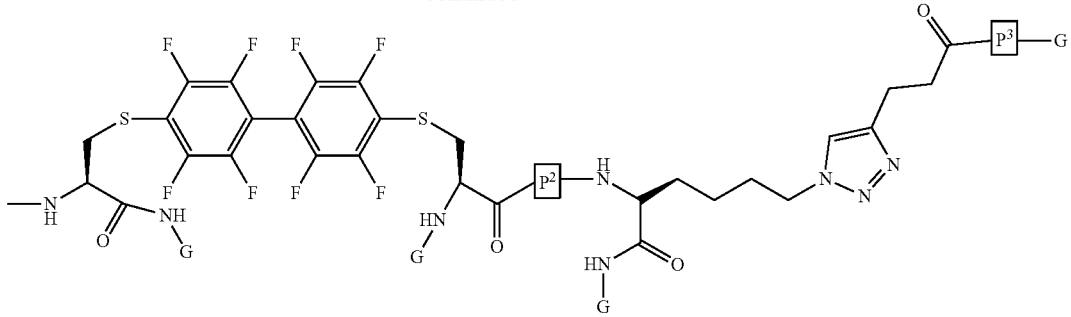

In one embodiment of the trimeric peptide-oligonucleotide-conjugates of the disclosure, G is H.

In another embodiment of the trimeric peptide-oligonucleotide-conjugates of the disclosure, G is —C(O)CH$_3$.

In some embodiments, the trimeric peptide-oligonucleotide-conjugates described herein are unsolvated. In other embodiments, one or more of the trimeric peptide-oligonucleotide-conjugates are in solvated form. As known in the art, the solvate can be any of pharmaceutically acceptable solvent, such as water, ethanol, and the like.

Although the trimeric peptide-oligonucleotide-conjugates of Formulae I, Ia, Ib, II, IIa and IV are depicted in their neutral forms, in some embodiments, these peptide-oligonucleotide-conjugates are used in a pharmaceutically acceptable salt form.

Oligonucleotides

Important properties of morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil, 5-methyl-cytosine and hypoxanthine) such that the polymer formed can hybridize with a complementary-base target nucleic acid, including target RNA, T$_M$ values above about 45° C. in relatively short oligonucleotides (e.g., 10-15 bases); 3) the ability of the oligonucleotide to be actively or passively transported into mammalian cells; and 4) the ability of the oligonucleotide and oligonucleotide:RNA heteroduplex to resist RNAse and RNase H degradation, respectively.

The stability of the duplex formed between an oligomer and a target sequence is a function of the binding T$_M$ and the susceptibility of the duplex to cellular enzymatic cleavage. The T$_M$ of an oligomer with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding T$_M$, with respect to a complementary-sequence RNA, of greater than body temperature and, in some embodiments greater than about 45° C. or 50° C. T$_M$s in the range 60-80° C. or greater are also included. According to well-known principles, the T$_M$ of an oligomer, with respect to a complementary-based RNA hybrid, can be increased by increasing the ratio of C:G paired bases in the duplex, or by increasing the length (in base pairs) of the heteroduplex, or both. At the same time, for purposes of optimizing cellular uptake, it may be advantageous to limit the size of the oligomer. For this reason, compounds of the disclosure include compounds that show a high T$_M$ (45-50° C. or greater) at a length of 25 bases or less.

The length of an oligonucleotide may vary so long as it is capable of binding selectively to the intended location within the pre-mRNA molecule. The length of such sequences can be determined in accordance with selection procedures described herein. Generally, the oligonucleotide will be from about 8 nucleotides in length up to about 50 nucleotides in length. For example, the length of the oligonucleotide (z) can be 8-38, 8-25, 15-25, 17-21, or about 18. It will be appreciated however that any length of nucleotides within this range may be used in the methods described herein.

In some embodiments, the antisense oligonucleotides contain base modifications or substitutions. For example, certain nucleo-bases may be selected to increase the binding affinity of the antisense oligonucleotides described herein. These include 5-substituted pyrimidines, 6-azapyrimidines and N-2, N-6 and 0-6 substituted purines, including 2-aminopropyladenine, 5-propynyluracil, 5-propynylcytosine and 2,6-diaminopurine. 5-methylcytosine substitutions have been shown to increase nucleic acid duplex stability by 0.6-1.2° C., and may be incorporated into the antisense oligonucleotides described herein. In one embodiment, at least one pyrimidine base of the oligonucleotide comprises a 5-substituted pyrimidine base, wherein the pyrimidine base is selected from the group consisting of cytosine, thymine and uracil. In one embodiment, the 5-substituted pyrimidine base is 5-methylcytosine. In another embodiment, at least one purine base of the oligonucleotide comprises an N-2, N-6 substituted purine base. In one embodiment, the N-2, N-6 substituted purine base is 2,6-diaminopurine.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

In an embodiment of Formula I, Ia, and Ib, R$^2$ is independently at each occurrence adenine, 2,6-diaminopurine, guanine, hypoxanthine, cytosine, 5-methyl-cytosine, thymine, uracil, and hypoxanthine; and each R$^1$ is —N(CH$_3$)$_2$.

Provided in Table 1 are various embodiments of nucleotide moieties as described herein.

TABLE 1

Various embodiments of nucleotide moieties.

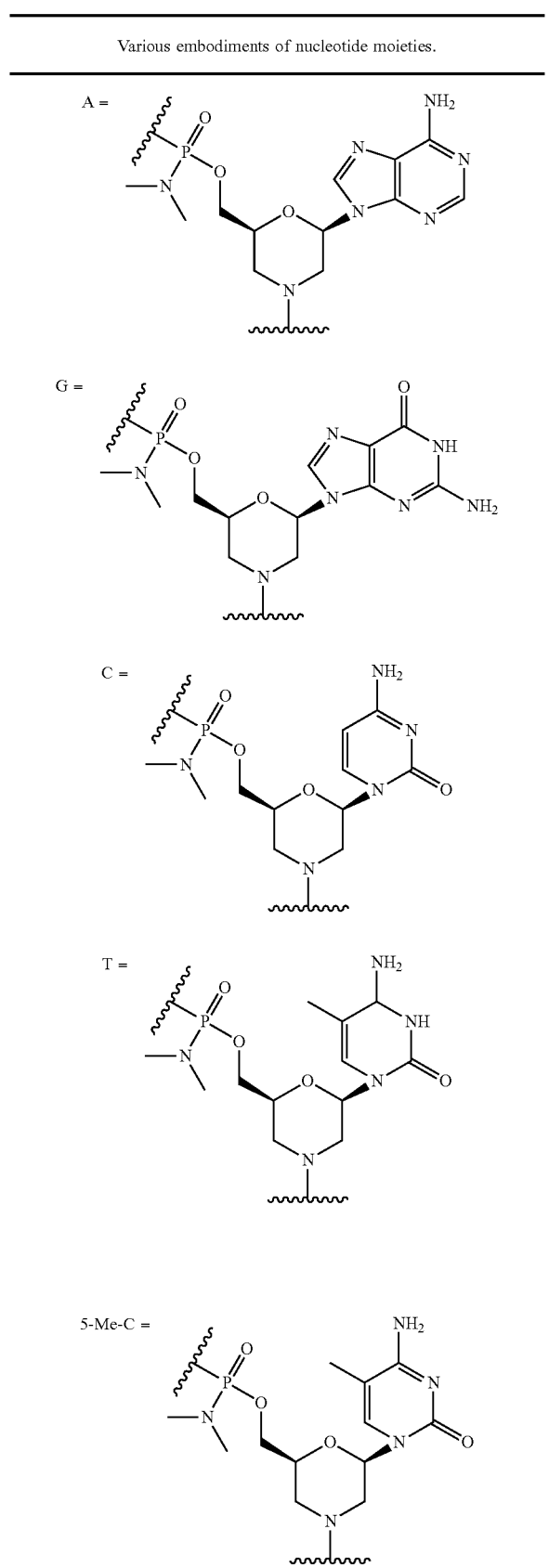

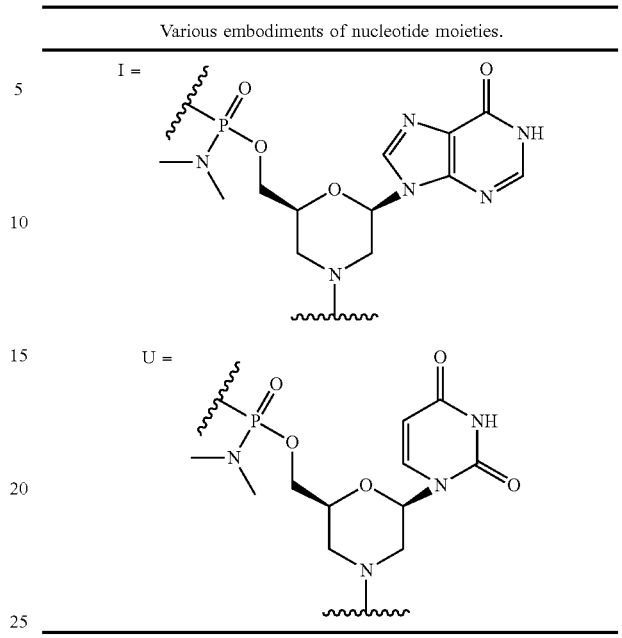

In a particular embodiment, the sequence listing for the oligonucleotide is GCTATTACCTTAACCCAG (SEQ ID. 56).

In some embodiments, the oligonucleotides described herein are unsolvated. In other embodiments, one or more of the oligonucleotides are in solvated form. As known in the art, the solvate can be any of pharmaceutically acceptable solvent, such as water, ethanol, and the like.

Although the oligonucleotides of Formulas I, Ia, and Ib, are depicted in their neutral forms, in some embodiments, these oligonucleotides are used in a pharmaceutically acceptable salt form.

Trimeric Peptides

The oligonucleotides provided herein include an oligonucleotide moiety conjugated to a trimeric peptide. In particular, the trimeric peptide comprises three covalently-linked cell-penetrating peptides, and wherein the three cell-penetrating peptides are independently an amphipathic peptide, a nuclear targeting peptide, an endosomal disrupting peptide, a chimeric peptide, a cyclic peptide, a bicyclic peptide, or an oligoarginine peptide.

In some embodiments, the three cell-penetrating peptides comprise one amphipathic peptide, one nuclear targeting peptide, and one additional cell-penetrating peptide, wherein the amphipathic peptide is the N-terminus of trimeric peptide, the nuclear targeting peptide is the middle peptide, and the additional cell-penetrating peptide is the C-terminus of trimeric peptide.

A representation of such a trimeric peptide is shown below:

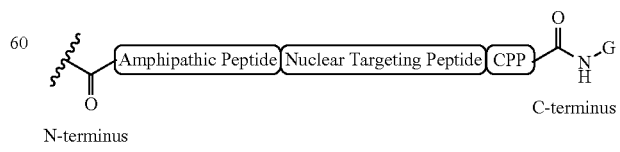

wherein the N-terminus is covalently attached to an oligonucleotide.

In some embodiments, the trimeric peptide can be effective to enhance transport of the compound into cells. The transport moiety is, in some embodiments, attached to a terminus of the oligomer. The peptides have the capability of inducing cell penetration within 30%, 40%, 50%, 60%, 70%, 80%, 90% or 100% of cells of a given cell culture population, including all integers in between, and allow macromolecular translocation within multiple tissues in vivo upon systemic administration.

The transport moieties as described above have been shown to greatly enhance cell entry of attached oligomers, relative to uptake of the oligomer in the absence of the attached transport moiety. Uptake may be enhanced at least three-fold, and, in some embodiments, 50-fold, relative to the unconjugated compound. In some embodiments, uptake may be enhanced, and, in some embodiments, three-fold, relative to the non-trimeric oligonucleotide-peptide conjugates.

The use of trimeric peptides are particularly useful in practicing the present disclosure. Certain trimeric peptide transporters have been shown to be highly effective at delivery of antisense compounds into primary cells including muscle cells. Furthermore, the trimeric peptide transporters described herein, when conjugated to an antisense PMO, demonstrate an enhanced ability to alter splicing of several gene transcripts.

Thus, in one aspect, provided herein is a trimeric peptide that is three covalently-linked cell-penetrating peptides, or a pharmaceutically acceptable salt thereof.

In an embodiment, each trimeric peptide is three covalently-linked cell-penetrating peptides, wherein the cell-penetrating peptides are independently an amphipathic peptide, a nuclear targeting peptide, an endosomal disrupting peptide, a chimeric peptide, a cyclic peptide, a bicyclic peptide, or an oligoarginine peptide.

In another embodiment, each trimeric peptide is three covalently-linked cell-penetrating peptides, wherein one of the cell-penetrating peptides is an amphipathic peptide, one of the cell-penetrating peptides is an nuclear targeting peptide, and one of the peptides is an additional cell-penetrating peptide.

In still another embodiment, each trimeric peptide is three covalently-linked cell-penetrating peptides, wherein the three cell-penetrating peptides comprise one amphipathic peptide, one nuclear targeting peptide, and one additional cell-penetrating peptide, and wherein the amphipathic peptide is the N-terminus of trimeric peptide, the nuclear targeting peptide is the middle peptides, and the addition cell-penetrating peptide is the C-terminus of trimeric peptide.

In still another embodiment, the amphipathic peptide comprises a hydrophobic peptidyl segment and a hydrophilic peptidyl segment, wherein the hydrophobic peptidyl segment comprises a sequence of 2 to 10 amino acids independently selected from glycine, isoleucine, alanine, valine, leucine, phenylalanine, tyrosine, or tryptophan, and wherein the hydrophilic peptidyl segment comprises a sequence of 2-20 amino acids independently selected from charged amino acids, uncharged but polar amino acids, or hydrophobic amino acids, wherein the hydrophilic peptidyl segment comprises at least one non-hydrophobic amino acid.

In an embodiment, the hydrophophilic peptidyl segment comprises a sequence of 2 to 20 amino acids independently selected from arginine, lysine, glutamine, asparagine, histidine, serine, threonine, tryptophan, alanine, isoleucine, leucine, methionine, phenylalanine, valine, proline, or glycine, wherein the hydrophilic peptidyl segment comprises at least one non-hydrophobic amino acid.

In another embodiment, $P^1$ is Penetratin, pVEC, TP10, or DPV6.

In yet another embodiment, $P^2$ is KRVK, SV40, or AAV-PHP.eB.

In a further embodiment, $P^3$ is DPV6, PPC3, PPC5, R12, R12 full cycle, R12 N-cycle, R12 C-cycle, R12 benzyl bicycle, R12 double cycle, Bpep, Bpep full cycle, Bpep C-cycle, Penetratin (nle), Engrailed N-cycle, Engrailed C-cycle, Engrailed full cycle, pVEC, pVEC-Bpep, AIP6 full cycle, Melittin-Bpep, Bh3 helix, Bac7, Buforin 2, Melittin, SynB1, S413-PVrev, Ribotoxin2 L3, PreS2-TLM, MAP, W/R, MAP12, SAP, SVM1, SVM3, SVM4, YTA4, 439a, HoxA13 serine2, Bip, PPR3, PPR4, AIP6, DPV15b, TAT, Penetratin, R9, HoxA13 serine1, KRVK TP10, TP10 KRVK, or SV40 TP10.

In an embodiment, $P^1$ is DPV6.

In another embodiment, $P^3$ is DPV6, Bpep, pVEC-Bpep, Buforin 2, SynB1, W/R, or AIP6.

In yet another embodiment, $P^1$ is DPV6, $P^2$ is SV40, and $P^3$ is DPV6, Bpep, pVEC-Bpep, Buforin 2, SynB1, W/R, or AIP6.

In a further embodiment, $P^1$ is DPV6, $P^2$ is SV40, and $P^3$ is pVEC-Bpep.

In an embodiment, $P^1$ is DPV6, $P^2$ is SV40, and $P^3$ is W/R.

In another embodiment, $P^1$ is DPV6, $P^2$ is SV40, and $P^3$ is SynB1.

Provided in Table 2 are various embodiments for variables PR, PC, and $P^3$:

TABLE 2

Various embodiments of CPPs.

| Peptide Name | Sequence | SEQ ID NO. |
|---|---|---|
| DPV6 | GRPRESGKKRKRKRLKP | 1 |
| PPC3 | KKYRGRKRHPR | 2 |
| PPC5 | GRKAARAPGRRKQ | 3 |
| R12 | RRRRRRRRRRRR | 4 |
| R12 full cycle | CRRRRRRRRRRRRC | 5 |
| R12 N-cycle | CRRRRRRCRRRRRR | 6 |
| R12 C-cycle | RRRRRRCRRRRRRC | 7 |
| R12 benzyl bicycle | CRRRRRRCRRRRRRC | 8 |
| R12 double cycle | CRRRRRRCCRRRRRRC | 9 |
| Bpep | RXRRBRRXRRBR | 10 |
| Bpep full cycle | CRXRRBRRXRRBRC | 11 |
| Bpep C-cycle | RXRRBRCRXRRBRC | 12 |
| Penetratin (nle) | RQIKIWFQNRRMKWKK | 13 |
| Engrailed N-cycle | CQIKIWFCNKRAKIKK | 14 |
| Engrailed C-cycle | SQIKIWFQCKRAKIKC | 15 |
| Engrailed full cycle | CSQIKIWFQNKRAKIKKC | 16 |
| pVEC | LLIILRRRIRKQAHAHSK | 17 |

TABLE 2-continued

Various embodiments of CPPs.

| Peptide Name | Sequence | SEQ ID NO. |
|---|---|---|
| pVEC-Bpep | LLIILRRRIRKQAHAHSKRXRRBR RXRRBR | 18 |
| AIP6 full cycle | Z*C*RLRWR*C* | 19 |
| Melittin-Bpep | GIGAVLKVLTTGLPALISWIKRKR QQRXRRBRRXRRBR | 20 |
| Bh3 helix | IWIAQELRRIGDEFNAYYARR | 21 |
| Bac7 | RRIRPRPPRLPRPRPRPLPFPRPG | 22 |
| Buforin 2 | TRSSRAGLQWPVGRVHRLLRK | 23 |
| Melittin | GIGAVLKVLTTGLPALISWIKRKR QQ | 24 |
| SynB1 | RGGRLSYSRRRFSTSTGR | 25 |
| S413-PVrev | ALWKTLLKKVLKAPKKKRKV | 26 |
| Ribotoxin2 L3 | KLIKGRTPIKFGKADCDRPPKHSQ NGMGK | 27 |
| PreS2-TLM | PLSSIFSRIGDP | 28 |
| MAP | KLALKALKALKAALKLA | 29 |
| W/R | RRWWRRWRR | 30 |
| MAP12 | LKTLTETLKELTKTLTEL | 31 |
| SAP | VRLPPPVRLPPPVRLPPP | 32 |
| SVM1 | FKIYDKKVRTRVVKH | 33 |
| SVM3 | KGTYKKKLMRIPLKGT | 34 |
| SVM4 | LYKKGPAKKGRPPLRGWFH | 35 |
| YTA4 | IAWVKAFIRKLRKGPLG | 36 |
| 439a | GSPWGLQHHPPRT | 37 |
| HoxA13 serine2 | RQVTIWSQNRRVKSKK | 38 |
| Bip | VSALK | 39 |
| PPR3 | PPRPPRPPR | 40 |
| PPR4 | PPRPPRPPRPPR | 41 |
| AIP6 | RLRWR | 42 |
| DPV15b | GAYDLRRRERQSRLRRRERQSR | 43 |
| TAT | RKKRRQRRR | 44 |
| Penetratin | RQIKIWFQNRRMKWKK | 45 |
| R9 | RRRRRRRRR | 46 |
| HoxA13 serine 1 | RSVTIWFQSRRVKEKK | 47 |
| KRVK TP10 | KRVKAGYLLGKINLKALAALAKKIL | 48 |
| TP10 KRVK | AGYLLGKINLKALAALAKKILKRVK | 49 |
| KRVK | KRVK | 50 |
| SV40 TP10 | PKKKRKVAGYLLGKINLKALAALAK KIL | 51 |
| TP10 | AGYLLGKINLKALAALAKKIL | 52 |
| SV40 | PKKKRKV | 53 |
| AAV-PHP.eB | SDGTLAVPFKA | 54 |
| PPC3 | KKYRGRKRHPR | 55 |

Bolded cysteines are linked with decafluorobiphenyl. Italic cysteines are linked with 1,3,5-trisbromomethylbenzene.

In some embodiments, the trimeric peptides described herein are unsolvated. In other embodiments, one or more of the chimeric peptides are in solvated form. As known in the art, the solvate can be any of pharmaceutically acceptable solvent, such as water, ethanol, and the like.

Although the trimeric peptides are depicted in their neutral forms, in some embodiments, these oligonucleotides are used in a pharmaceutically acceptable salt form.

Methods

Provided herein are methods of treating a neuromuscular disease, a muscle disease, a viral infection, or a bacterial infection in a subject in need thereof, comprising administering to the subject a peptide-oligonucleotide-conjugate of Formulae I, Ia, or Ib.

Accordingly, in one aspect, provided herein is a method of treating a muscle disease, a viral infection, a neuromuscular disease or a bacterial infection in a subject in need thereof, comprising administering to the subject a chimeric peptide-oligonucleotide-conjugate of the present disclosure.

In one embodiment, the neuromuscle disease is Duchenne Muscular Dystrophy.

In another embodiment, the viral infection is caused by a virus selected from the group consisting of marburg virus, ebola virus, influenza virus, and dengue virus.

In another embodiment, the bacterial infection is caused by *Mycobacterium tuberculosis*.

The subject considered herein is typically a human. However, the subject can be any mammal for which treatment is desired. Thus, the methods described herein can be applied to both human and veterinary applications.

Administration/Dose

The formulation of therapeutic compositions and their subsequent administration (dosing) is within the skill of those in the art. Dosing is dependent on severity and responsiveness of the disease state to be treated, with the course of treatment lasting from several days to several months, or until a sufficient diminution of the disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 μg to 100 g/kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 µg to 100 g/kg of body weight, once or more daily, to once every 20 years.

In some embodiments, the trimeric conjugate of Formulae I, Ia, or Ib is administered alone.

In some embodiments, the trimeric conjugate of Formulae I, Ia, or Ib is administered in a therapeutically effective amount or dosage. A "therapeutically effective amount" is an amount of the trimeric conjugate of Formulae I, Ia, or Ib that, when administered to a patient by itself, effectively treats a muscle disease, a viral infection, or a bacterial infection. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the oligonucleotide that corresponds to a therapeutically effective amount is strongly dependent on the type of disease, stage of the disease, the age of the patient being treated, and other facts.

In different embodiments, depending on the trimeric conjugate of Formulae I, Ia, or Ib and the effective amounts used, the oligonucleotides can modulate the expression of a gene involved in a muscle disease, a viral infection, or a bacterial infection.

While the amounts of the trimeric conjugate of Formulae I, Ia, or Ib should result in the effective treatment of a muscle disease, a viral infection, or a bacterial infection, the amounts, are preferably not excessively toxic to the patient (i.e., the amounts are preferably within toxicity limits as established by medical guidelines). In some embodiments, either to prevent excessive toxicity or provide a more efficacious treatment, or both, of a muscle disease, a viral infection, or a bacterial infection, a limitation on the total administered dosage is provided. Typically, the amounts considered herein are per day; however, half-day and two-day or three-day cycles also are considered herein.

Different dosage regimens may be used to treat a muscle disease, a viral infection, or a bacterial infection. In some embodiments, a daily dosage, such as any of the exemplary dosages described above, is administered once, twice, three times, or four times a day for three, four, five, six, seven, eight, nine, or ten days. Depending on the stage and severity of the disease being treated, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

The trimeric conjugate of Formulae I, Ia, or Ib, or their pharmaceutically acceptable salts or solvate forms, in pure form or in an appropriate pharmaceutical composition, can be administered via any of the accepted modes of administration or agents known in the art. The oligonucleotides can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, for example, in unit dosage forms suitable for simple administration of precise dosages. A particular route of administration is oral, particularly one in which a convenient daily dosage regimen can be adjusted according to the degree of severity of the disease to be treated.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active oligonucleotide or oligonucleotides in a certain part of the intestinal tract in a delayed manner. Examples of embedded compositions that can be used are polymeric substances and waxes. The active oligonucleotides also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the conjugates described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the oligonucleotides described herein, or a pharmaceutically acceptable salt thereof, and 99% to 1% by weight of a pharmaceutically acceptable excipient. In one example, the composition will be between about 5% and about 75% by weight of a oligonucleotide described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits according to the disclosure include package(s) comprising oligonucleotides, peptides, peptide-oligonucleotide-conjugates, or compositions of the disclosure. In some embodiments, kits comprise a peptide-oligonucleotide-conjugate according to Formulae I, Ia, or Ib, or a pharmaceutically acceptable salt thereof.

The phrase "package" means any vessel containing oligonucleotides or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering oligonucleotides or compositions of the disclosure to a patient. Kits also can comprise instructions for approved uses of oligonucleotides herein by regulatory agencies, such as the United States Food and Drug Administration. Kits can also contain labeling or product inserts for the oligonucleotides. The package(s) or any product insert(s), or both, may themselves be approved by regulatory agencies. The kits can include oligonucleotides in the solid phase or in a liquid phase (such as buffers provided) in a package. The kits can also include buffers for preparing solutions for conducting the methods, and pipettes for transferring liquids from one container to another.

Process for Preparing Trimeric Peptide-Oligonucleotide-Conjugates

In another aspect, provided herein is a process for preparing the trimeric peptide-oligonucleotide-conjugates described in this application. In particular, provided herein is a process for preparing a trimeric peptide-oligonucleotide conjugate of Formula (II):

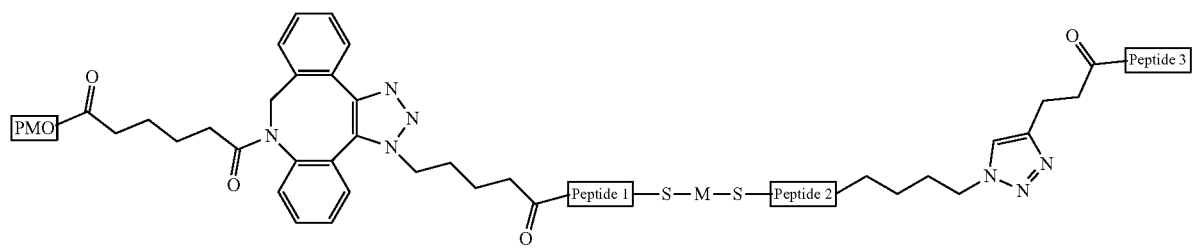

(II)

comprising:
(a) contacting a compound of Formula (III)

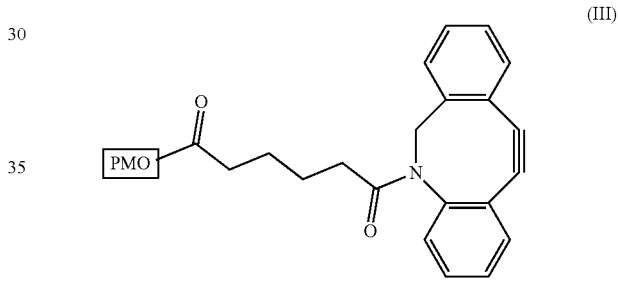

(III)

with a compound of Formula (IV)

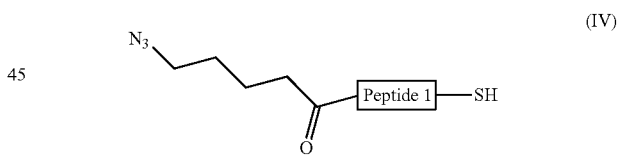

(IV)

in the presence of an acid to form a compound of Formula (V)

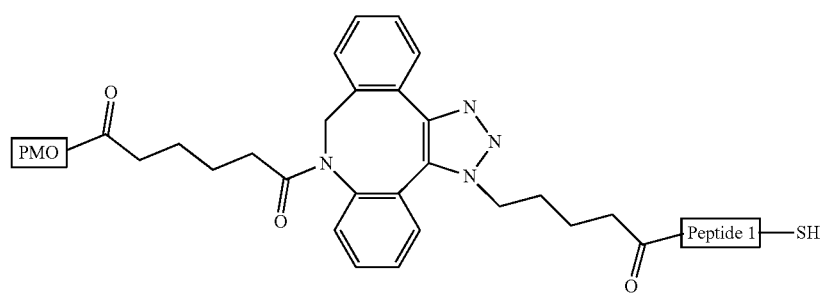

(V)

(b) contacting a compound of Formula (VI)

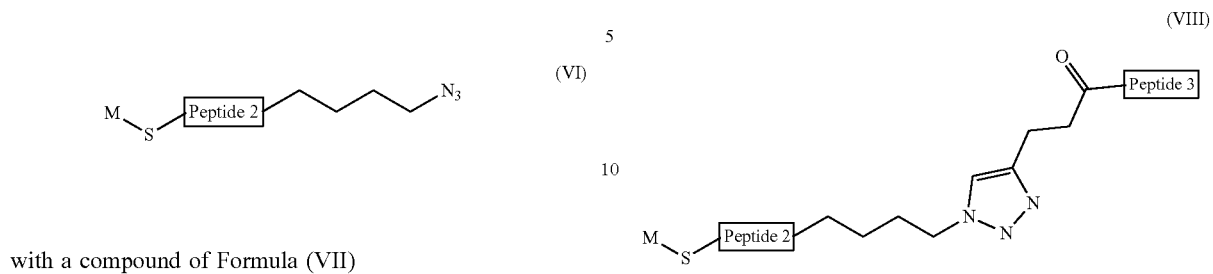

with a compound of Formula (VII)

in the presence of a copper catalyst to form a compound of Formula (VIII)

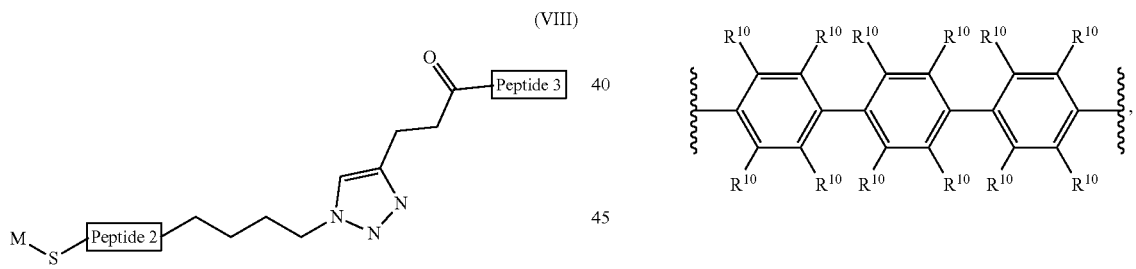

(c) contacting a compound of Formula (V)

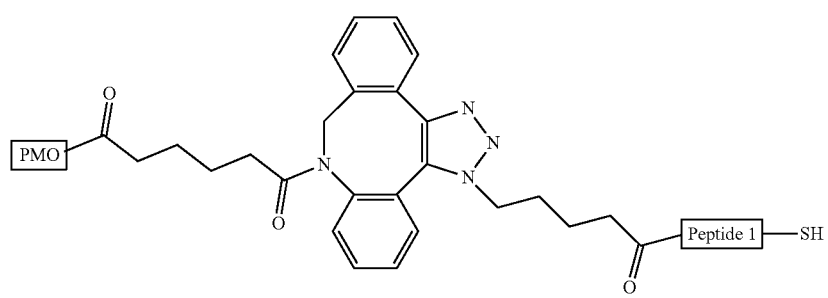

with a compound of Formula (VIII) in the presence of a coupling reagent to form a compound of Formula (II);

wherein M is and $R^{10}$ is independently at each occurrence H or a halogen, wherein M is covalently-linked to the side chain of a terminal or internal cysteine on $P^1$ and $P^2$;

wherein the PMO is an oligonucleotide of Formula IX:

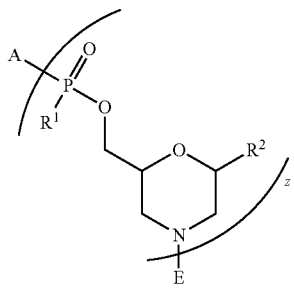

(IX)

or a pharmaceutically acceptable salt thereof,
wherein
A is selected from the group consisting of OH, —NHCH$_2$C(O)NH$_2$, —N(C$_{1-6}$-alkyl)CH$_2$C(O)NH$_2$,

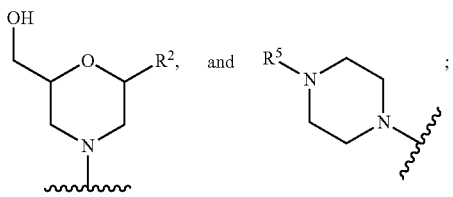

R$^5$ is —C(O)(O-alkyl)$_x$OH, wherein x is 3-10 and each alkyl group is independently at each occurrence —C$_{2-6}$-alkyl, or R$^5$ is selected from the group consisting of —C(O)C$_{1-6}$-alkyl, trityl, monomethoxytrityl, —C$_{1-6}$-alkyl-R$^6$, —C$_{1-6}$-heteroalkyl-R$^6$, -aryl-R$^6$, -heteroaryl-R$^6$, —C(O)O—C$_{1-6}$-alkyl-R$^6$, —C(O)O-aryl-R$^6$, and —C(O)O-heteroaryl-R$^6$, or R$^5$ is the attachment point for the trimeric peptide;

R$^6$ is selected from the group consisting of OH, SH, and NH$_2$, or R$^6$ is O, S, or NH, covalently linked to a solid support;

each R$^1$ is independently OH or —NR$^3$R$^4$;

each R$^3$ and R$^4$ are independently at each occurrence —C$_{1-6}$-alkyl;

each R$^2$ is independently selected from the group consisting of H, a nucleobase, and a nucleobase functionalized with a chemical protecting-group, wherein the nucleobase independently at each occurrence comprises a C$_{3-6}$-heterocyclic ring selected from the group consisting of pyridine, pyrimidine, triazinane, purine, and deaza-purine;

z is 8-40;

E is selected from the group consisting of H, —C$_{1-6}$-alkyl, —C(O)C$_{1-6}$-alkyl, benzoyl, stearoyl, trityl, monomethoxytrityl, dimethoxytrityl, trimethoxytrityl, and

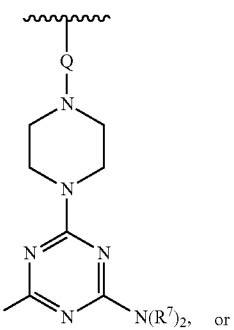

E is the attachment point for the trimeric peptide;
Q is —C(O)(CH$_2$)$_6$C(O)— or —C(O)(CH$_2$)$_2$S$_2$(CH$_2$)$_2$C(O)—;
R$^7$ is —(CH$_2$)$_2$OC(O)N(R$^8$)$_2$; and
R$^8$ is —(CH$_2$)$_6$NHC(=NH)NH$_2$.

In an embodiment, the acid of step (a) is trifluoroacetic acid.

In another embodiment, the copper catalyst of step (b) is copper (I) bromide.

In yet another embodiment, the coupling reagent of step (c) is Tris(2-carboxyethyl)phosphine hydrochloride (TCEP).

In a further embodiment, the solvent for step (a) is water, the solvent for step (b) is water/DMSO, and the solvent for step (c) is water/DMSO.

In another embodiment, the products of steps (a) and (b) are inert to the reaction conditions of step (c).

In another embodiment, the products of steps (a) and (b) can be used in step (c) without any purification.

EXAMPLES

Examples have been set forth below for the purpose of illustration and to describe certain specific embodiments of the disclosure. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations or methods of the disclosure may be made without departing from the spirit of the disclosure and the scope of the appended claims. Definitions of the variables in the structures in the schemes herein are commensurate with those of corresponding positions in the formulae presented herein.

Figure 2:
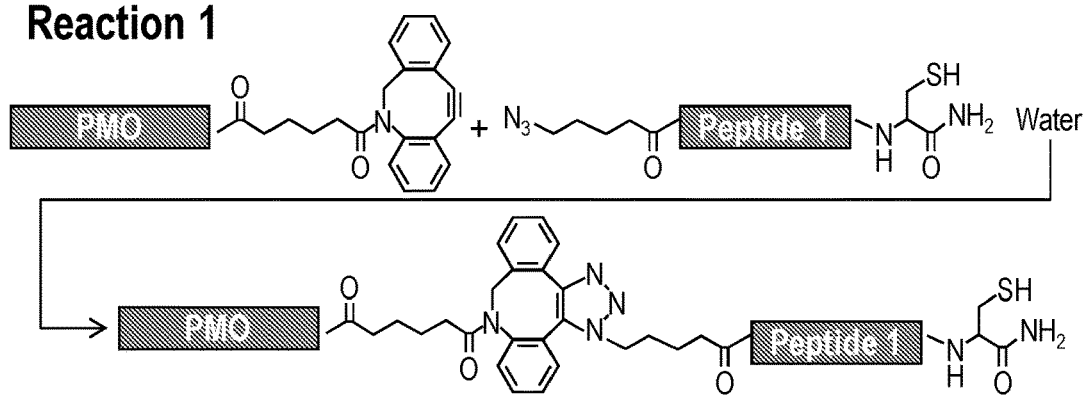
FIG. 2 shows the synthetic scheme for the synthesis of a modular construct.
Figure 2:
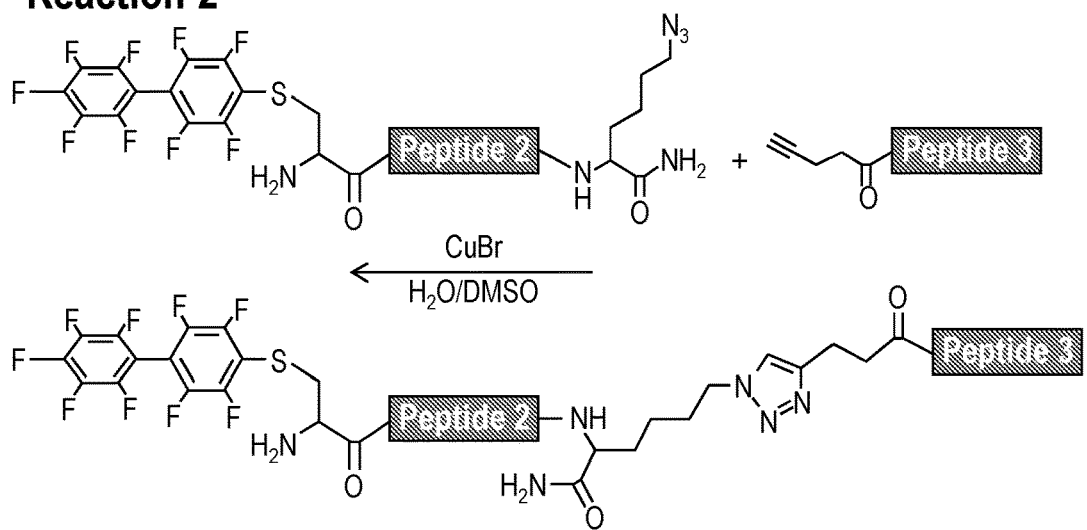
Figure 2:
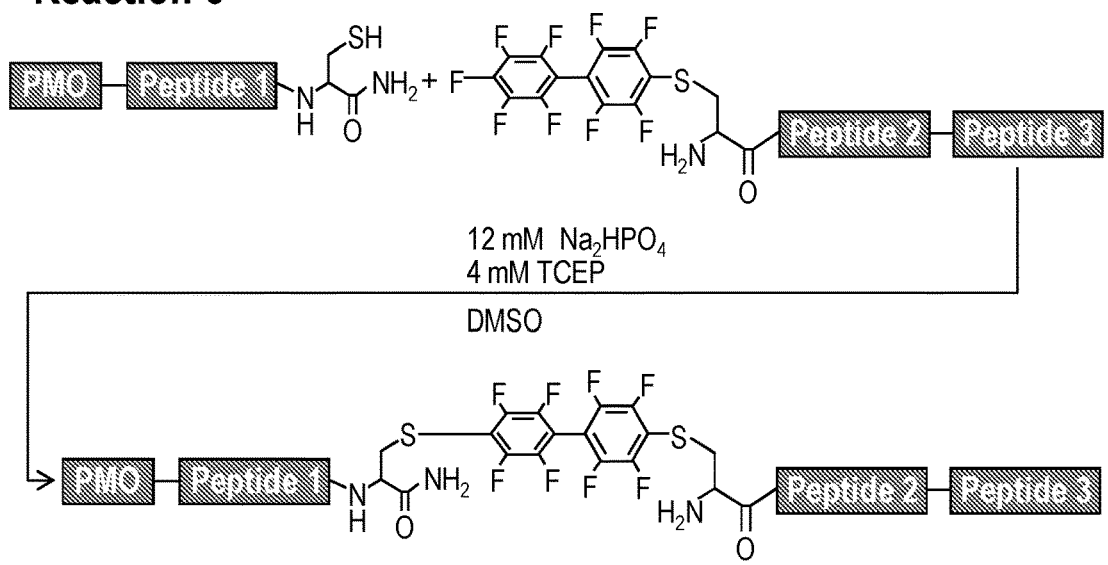

Focus was placed on constructs containing four modules: one for the oligonucleotide and three for distinct peptide sequences. It was envisioned that it would be necessary for the modules to contain a variety of functional peptides, such as nuclear targeting peptides or endosomal disrupting peptides. To synthesize the constructs, a convergent approach was chosen, in which the Module 1 was linked to Module 2 and separately Module 3 was linked to Module 4. Then, the two dimers could be conjugated to provide a four-module construct (FIG. 2).

The choice of bioconjugation reactions was critical, as each reaction needed to be optimized to be tolerant of certain functional groups, compatible with common solvents and conditions, and suitable for peptide substrates. Several reactions were explored in the context of peptide conjugation and various limitations for certain reactions were encountered.

TABLE 3

List of functional groups used for common bioconjugation reactions, and the potential constraints on their use.

| Functional Group | Conjugation Constraints |
| --- | --- |
| Thiol | Can require reducing agent to prevent disulfide formation |
| | Can react with DBCO |
| Maleimide | Reacts with azides |
| | Linkage is reversible |
| Alkyl Halide | Slow rate of reaction with thiols |
| Perfluoroarene | Unstable linkage above pH 10 |
| | Hydrophobic |
| Tetrazine | Reduces rapidly in presence of thiol or TIPS |
| | Reacts with DBCO |
| Norbornene | Reacts with thiols during peptide cleavage |
| | Reacts with azides |
| DBCO | Reacts with tetrazine, can react with thiols |
| | Linker hydrolyzed in the presence of trifluoroacetic acid |
| Aldehyde | Intrinsically reversible |
| Alkyne | Reacts with palladium (e.g. during alloc removal) |
| Azide | Reduced by TCEP |

For example, it was found that tetrazines can be incorporated into a peptide on resin but are reduced during peptide cleavage and side-chain deprotection. Similarly, the tertiary amide present on commercially available DBCO reagents is cleaved in trifluoroacetic acid, requiring the incorporation of DBCO to substrates off-resin. Additionally, maleimides and azides will react when present on the same peptide.

After investigating several potential reactions, the final synthetic scheme combines two azide-alkyne cycloadditions with one $S_NAr$ reaction (FIG. 2). In reaction 1, a PMO-DBCO will couple with an azido peptide to link modules 1 and 2. The azido peptide will also contain a free thiol, which under neutral conditions, will not react with DBCO. Separately, for reaction 2, a copper-catalyzed azide-alkyne cycloaddition will link modules 3 and 4. Module 3 will contain N-terminal cysteine residue linked to decafluorobiphenyl and a C-terminal azido-lysine. The perfluoroarene enables reaction 3 and also serves to prevent a free thiol from interfering with the azide/alkyne cycloaddition. Module 4 only contains an alkyne, which is stable towards most reactions, such as peptide macrocyclization. Lastly, in reaction 3, module 1-2 and 3-4 can be conjugated through a thiol-perfluoroarene $S_NAr$ reaction. Because the azides have already reacted with the alkynes, TCEP can be used to prevent disulfide formation without worrying about unintentional azide reduction.

The chosen synthetic scheme has numerous benefits for the synthesis of a combinatorial library. First, all reactions have been used in biological assays before to generate stable, irreversible linkages. Second, the reactions do not generate side-products and are theoretically quantitative, which reduces the need for purification. Third, all of the reagents are relatively benign and should not affect cell culture experiments. Although copper will be present, it was found that low micromolar concentrations of copper did not affect cell viability for the purposes of this screen. Lastly, the reactions can all be conducted at very small scale (e.g. volumes less than 5 μL). Notably, the combination of high yield and small volume suggests that the reactions can be performed at high concentrations and immediately diluted into media for cell culture treatment, without the need to purify each reaction individually.

After optimizing the individual reaction conditions, a set of 36 proof-of-concept constructs were synthesized. For the oligonucleotide, module 1, PMO IVS2-654 (SEQ. ID. 56), which upon successful delivery to the nucleus in a modified HeLa cell line, induces eGFP fluorescence was used. Module 2 included a set of four different CPPs: penetratin, pVEC, TP10, and DPV6. Module 3 included the KRVK and SV40 nuclear localization sequences (NLS) and the peptide PHP.eB, a sequence recently reported to improve viral delivery into the brain. Module 4 included three CPPs: Bpep, DPV6, and PPC3 (FIG. 3).

The synthesis began with the conjugation of modules 1 and 2 using an azide-strained-alkyne cycloaddition. In water, 5 mM PMO-DBCO was incubated with 5 mM azide-module 2 peptide-cys. After one hour, the reaction was flash frozen in liquid nitrogen and the solvent was removed by lyophilization. For each reaction, LC-MS analysis showed nearly complete conversion to the product and indicated that the reaction proceeded cleanly with no need for purification.

Modules 3 and 4 were conjugated using copper-catalyzed azide-alkyne cycloaddition. The decafluorobiphenyl-module 3 peptide-azide and alkyne-module 4 peptide were dissolved in water to make a 10 mM stock solution of each module. Separately, copper (I) bromide was dissolved in DMSO under an inert atmosphere. The peptides were combined (final concentration of 3.3 mM each) and the reaction was initiated with the addition of copper bromide solution (final concentration 6.7 mM). After 2 hours, the reaction was quenched with the addition of 100 mM disodium phosphate in water. In preparation for reaction 3, the solvent was removed under vacuum.

Lastly, modules 1-2 and 3-4 were combined. Module 1-2 (final concentration 0.63 mM) was mixed with Module 3-4 (final concentration 1.25 mM, 2 equivalents) in DMSO containing 5 mM TCEP. Because Module 1 is the active component for cellular assays, it was used as the limiting reagent. After 2 hours, the reaction was flash frozen and stored at −80° C. until dilution and cell treatment. Testing the reaction components individually suggests that the presence of copper interferes with the reaction, and despite substantial attempts at optimization, reaction conversion never exceeded approximately 70%.

With the 36 constructs synthesized, the ability to modulate PMO activity using the modified HeLa cell assay was tested. The HeLa-654 cells were stably transfected to express a nonfluorescent eGFP protein. The eGFP gene is interrupted by a mutant intron from the human β-globin gene (IVS2-654). The insertion alters pre-mRNA splicing to cause retention of a fragment in the mature mRNA that results in a nonfluorescent protein. PMO IVS2-654 base-pairs with the β-globin insertion, modifies mRNA splicing, and thereby leads to expression of fluorescent eGFP.

For treatment, the crude reaction mixture was diluted to 5 μM in media. The concentration of the modular construct was calculated based on the original concentration of the module 1-2 conjugate mixed in the reaction. Using media containing 10% fetal bovine serum (FBS), the cells were treated with each construct for 22 hours, after which the cellular fluorescence was measured by flow cytometry.

Figure 4:
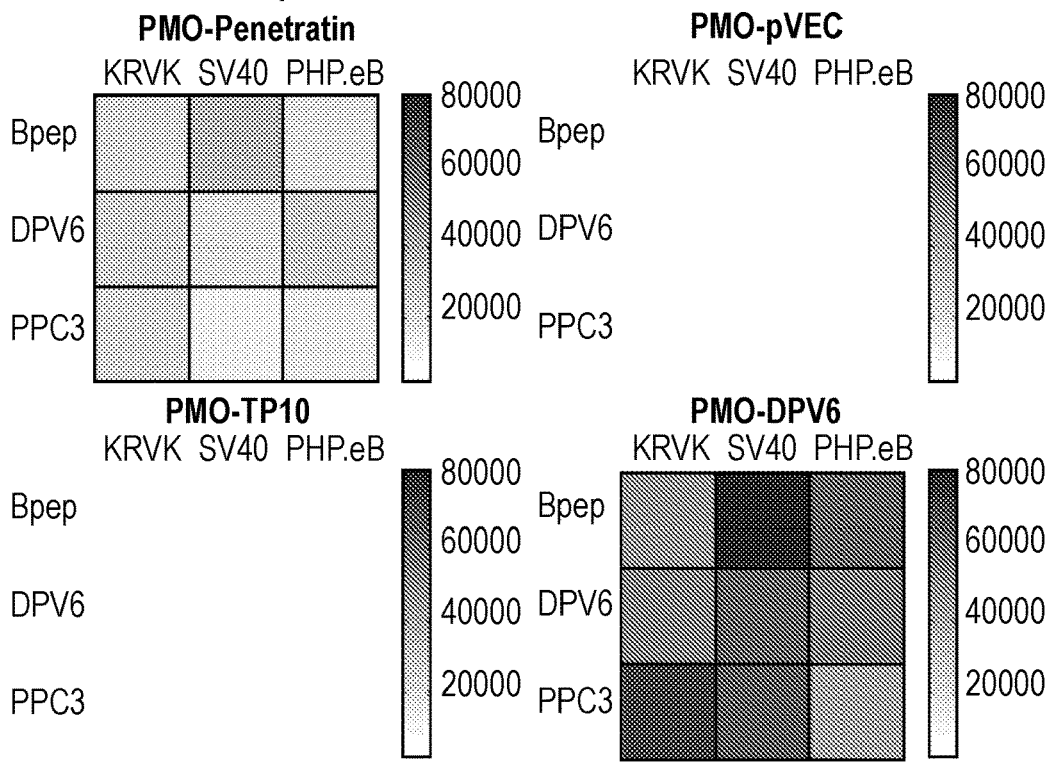
FIG. 4 A) shows heat maps disclosing the mean cellular fluorescence of HeLa-654 cells treated with each modular construct (n=3 replicate wells). B) Shows heat maps disclosing the total cell count of HeLa-654 cells after treatment with each modular construct. Each experiment was capped at 5000 cells. Low cell counts suggest cytotoxicity. C) Shows heat maps disclosing the cell count multiplied by the mean fluorescence (F×C) which gives a single metric that captures the two most important parameters for a modular construct.
Figure 4:
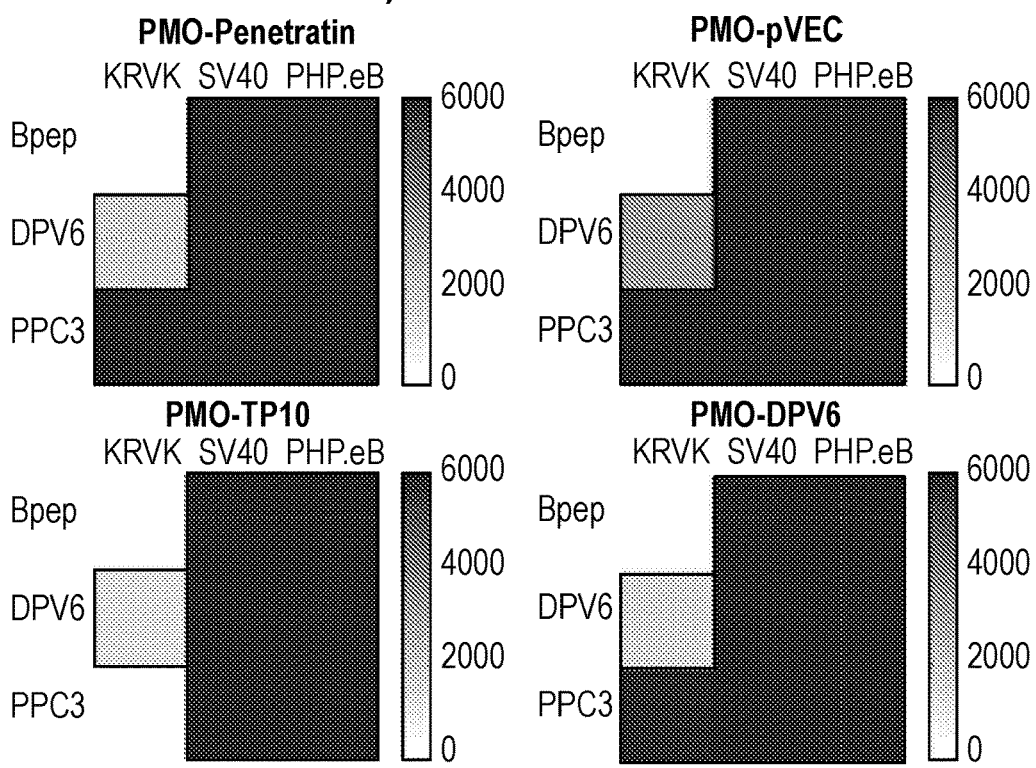
Figure 4:
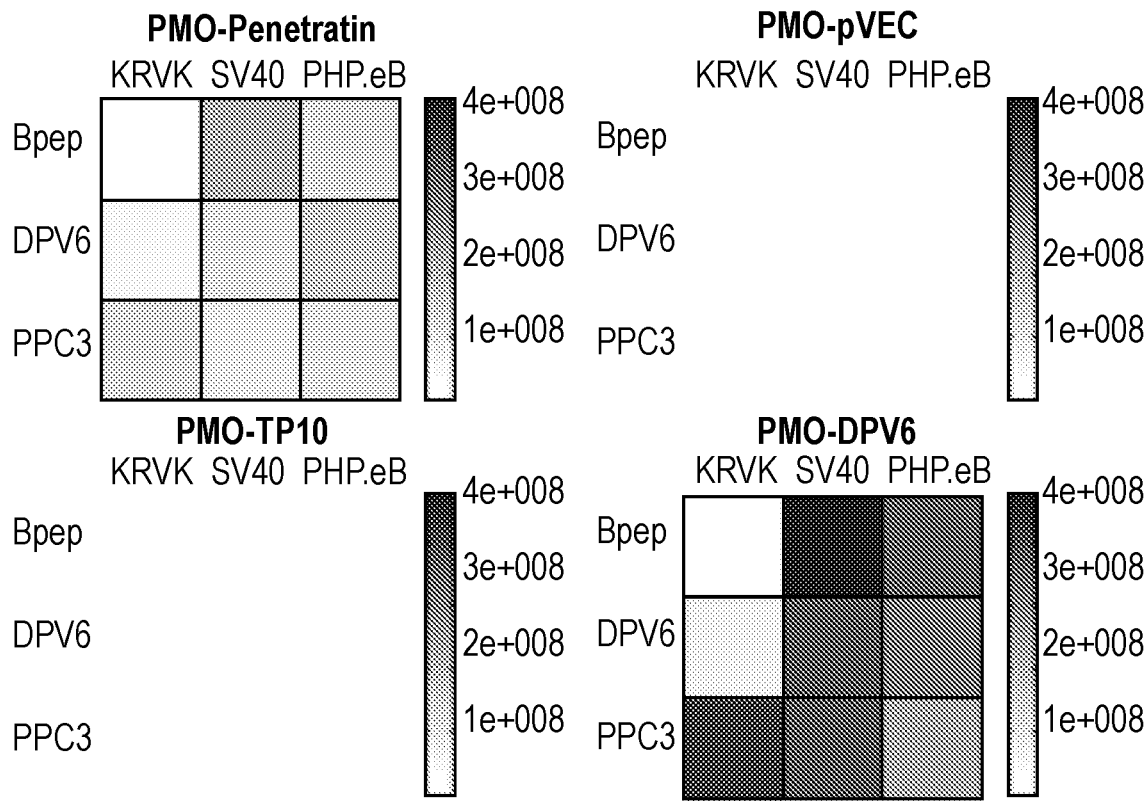

The different modules led to several noticeable trends in the level of cellular fluorescence (FIG. 4). When module 2 was DPV6, the overall construct consistently led to high fluorescence, regardless of which peptides were placed in module 3 and 4. However, when either pVEC or TP10 was placed in module 2, minor cellular fluorescence was observed. We used the gated cell count during flow cytometry as an indirect read-out to control for the toxicity of the compounds. Highly toxic compounds led to a reduction in overall cell count and non-viable cells were gated out based upon propidium iodide staining. In this experiment, it was observed that when the module 3 peptide was the nuclear localization sequence KRVK, lower cell counts were consistently observed. Since preferred compounds are both highly active and nontoxic, the cell fluorescence and cell count readings were multiplied together to obtain a measure of overall compound efficacy (F×C).

Given the success of the proof-of-concept experiment, a library of 600 conjugates for testing in the HeLa-654 cells was synthesized. It was chosen to increase the number of peptides in module 4 from 3 to 50. To increase the diversity of the types of peptides in the library and highlight the feasibility of incorporating modified peptides and unusual functional groups, a mixture of chimeric peptides, cyclic peptides, and bicyclic peptides were included. The cyclic peptides included R12, Bpep, and Engrailed variants in which two cysteine residues were linked to form a stable peptide macrocycle that are compatible with the modular reactions. The bicyclic variants included a double macrocyclic R12 and another R12 sequence where three side-chains were linked with 1,3,5-trisbromomethylbenzene. The other peptides included several previous reported CPPs, peptides computationally predicted to be effective PMO carriers (PPCs), and peptides with an appended NLS sequence (see Table 2.)

Figure 5:
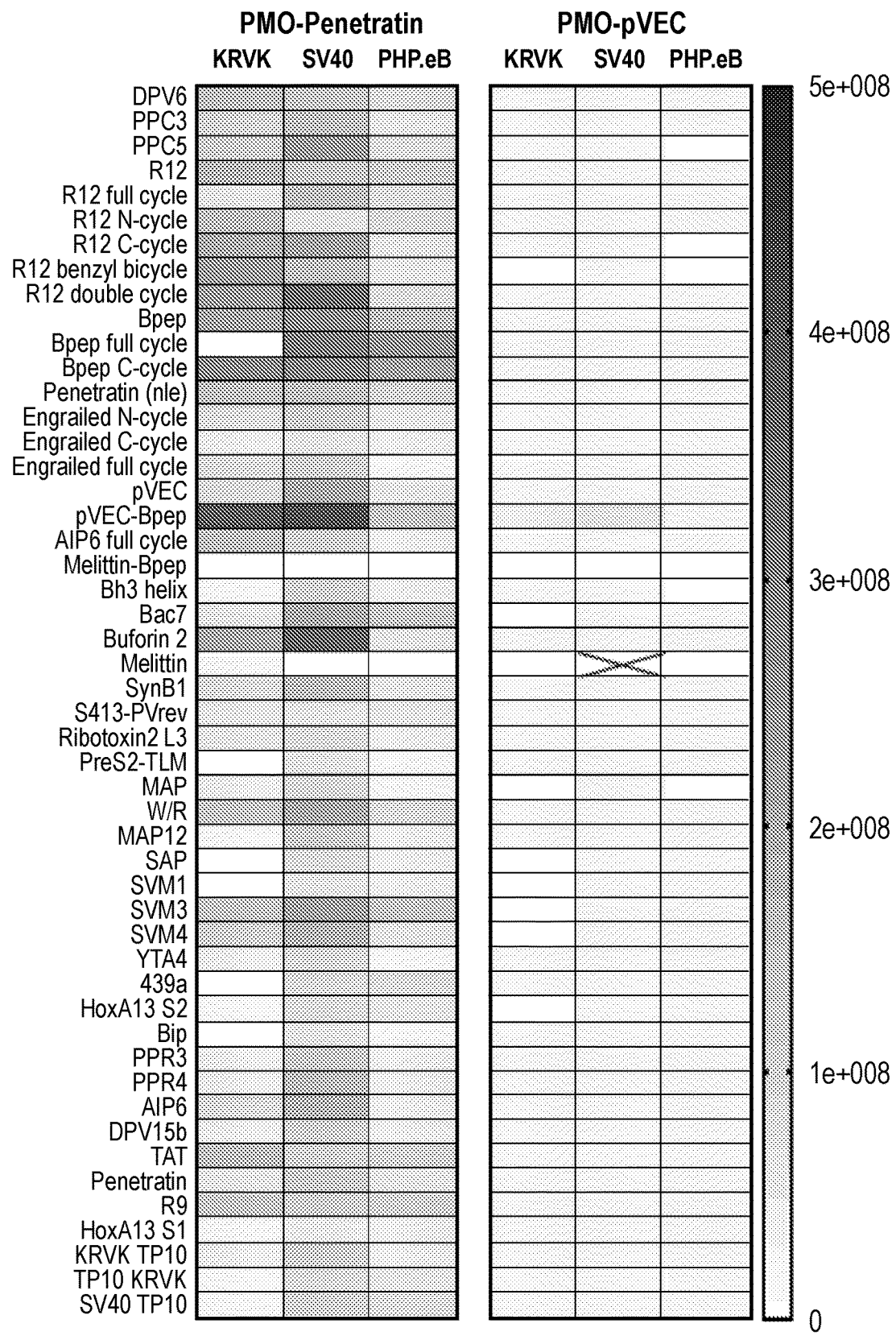
FIG. 5 shows heat maps disclosing the F×C of the 600 constructs tested in the HeLa-654 assay (n=1 replicate well). The most potent compound was PMO-DPV6-SV40-W/R, a combination of peptides that, prior to testing, would not have been predicted to be particularly notable. Boxes marked with an "X" are constructs in which the gated cell count was zero.
Figure 5:
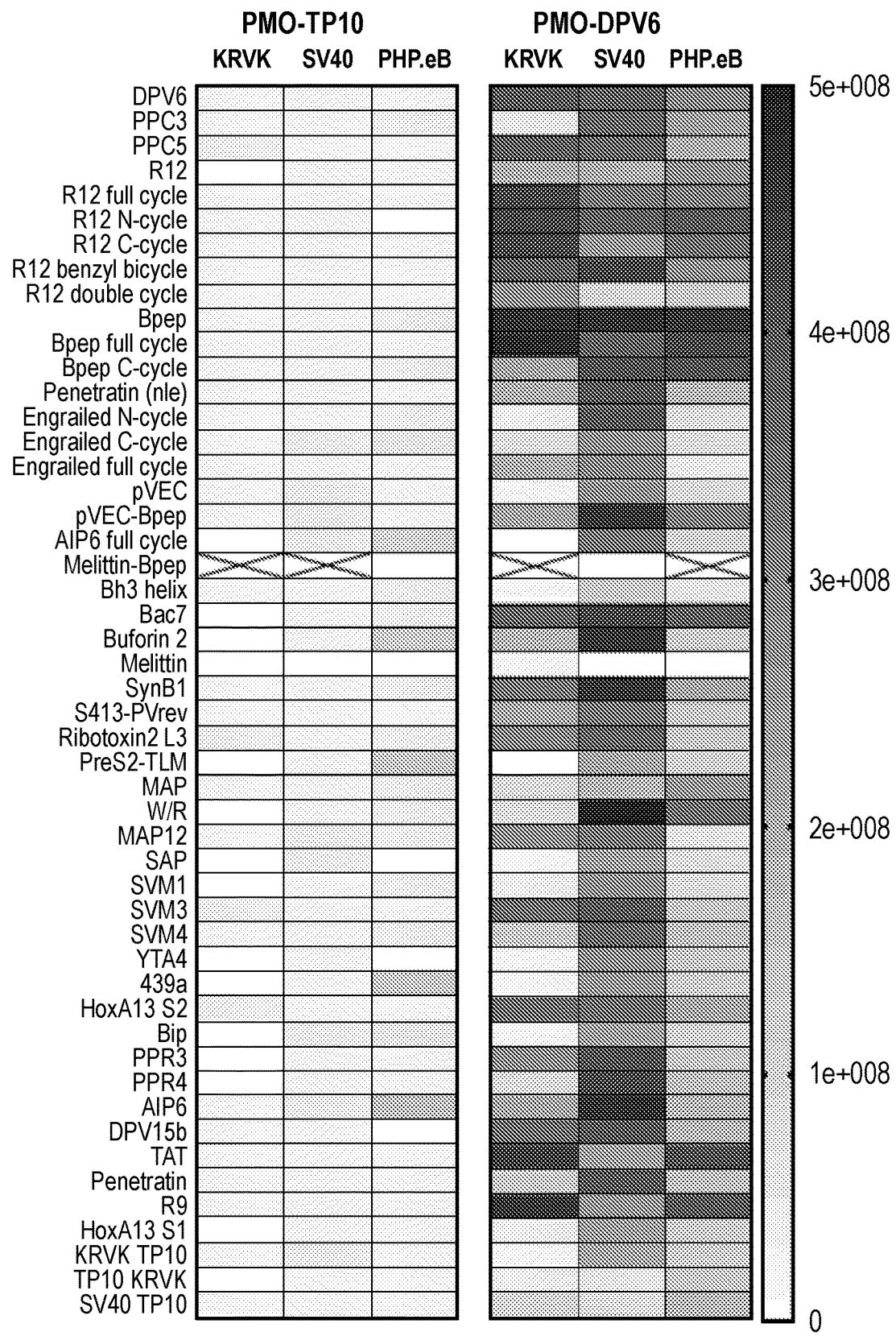

With the additional compounds, reactions 1 and 2 were carried out as previously described, except reaction 2 now involved 150 distinct products. For reaction 3, to handle the large number of compounds, the synthesis was carried out over two days in 384 well plates, using the previously-described conditions. After synthesis, the compounds were diluted to 100 µM in PBS, and then to 5 µM in media containing 10% FBS. Again, HeLa-654 cells were treated with the construct for 22 hours and the cellular fluorescence was analyzed by flow cytometry (FIG. 5).

The different peptide combinations highlighted certain trends in peptide efficacy. First, as seen in the proof-of-concept experiment, DPV6 as module 2 leads to highest F×C. For module 4, the pVEC-Bpep chimera consistently lead to high performance. Certain conjugates were highly toxic when the module 4 position contained peptides such as melittin or melittin-Bpep. As predicted, highly cationic peptides, such as R12 or Bpep variants, are relatively more active and cluster at the top of the heat map. Lastly, the role of individual modules is critical—as shown for module 2 peptides, the presence of pVEC or TP10 reduces the fluorescence dramatically and contributes the dominant effect, even though certain peptides in modules 3 and 4 can tune the fluorescence up or down.

PMO-DPV6-SV40-W/R was the top hit with the highest overall F×C. The gated cell count reached the maximum of 5000 cells and the mean fluorescence intensity was approximately 20-fold higher than unconjugated PMO. Because W/R was not a particularly potent peptide when conjugated to PMO on its own (around 3× as active as PMO by itself) this result provides further support to the notion that combining multiple peptides is beneficial. One intriguing trend shows that W/R, in addition to the peptides buforin 2 and synB1, performs exceptionally well when first three modules contain PMO-DPV6-SV40. These three peptides are less potent when module 3 contains the peptides KRVK or PHP.eB. Without being bound by a particular theory, this may stem from the greater net charge provided by SV40, plenty of constructs (e.g. PMO-DPV6-SV40-R12) have a higher net positive charge yet lower activity.

Example 1: General Method for Peptide Preparation and Purification

Fast-Flow Peptide Synthesis

Peptides were synthesized on a 0.1-mmol scale using an automated flow peptide synthesizer. A 200 mg portion of ChemMatrix Rink Amide HYR resin was loaded into a reactor maintained at 90° C. All reagents were flowed at 80 mL/min with HPLC pumps through a stainless-steel loop maintained at 90° C. before introduction into the reactor. For each coupling, 10 mL of a solution containing 0.2 M amino acid and 0.17 M HATU in DMF were mixed with 200 µL diisopropylethylamine and delivered to the reactor. Fmoc removal was accomplished using 10.4 mL of 20% (v/v) piperidine. Between each step, DMF (15 mL) was used to wash out the reactor. Special coupling conditions were used for arginine, in which the flow rate was reduced to 40 mL/min and 10 mL of a solution containing 0.2 M Fmoc-L-Arg(Pbf)-OH and 0.17 M PyAOP in DMF were mixed with 200 µL diisopropylethylamine and delivered to the reactor. To couple unnatural amino acids or to cap the peptide (e.g. with 4-pentynoic acid), the resin was incubated for 30 min at room temperature with 4-pentynoic acid (1 mmol) dissolved in 2.5 mL 0.4 M HATU in DMF with 500 µL diisopropylethylamine. After completion of the synthesis, the resin was washed 3 times with DCM and dried under vacuum.

Peptide Cleavage and Deprotection

Each peptide was subjected to simultaneous global side-chain deprotection and cleavage from resin by treatment with 5 mL of 94% trifluoroacetic acid (TFA), 2.5% 1,2-ethanedithiol (EDT), 2.5% water, and 1% triisopropylsilane (TIPS) (v/v) for 7 min at 60° C. For arginine-rich sequences, the resin was treated with a cleavage cocktail consisting of 82.5% TFA, 5% phenol, 5% thioanisole, 5% water, and 2.5% EDT (v/v) for 14 hours at room temperature. The TFA was evaporated by bubbling N2 through the mixture. Then ~40 mL of cold ether (chilled at −80° C.) was added to precipitate and wash the peptide. The crude product was pelleted through centrifugation for three minutes at 4,000 rpm and the ether decanted. The ether precipitation and centrifugation were repeated two more times. After the third wash, the pellet was redissolved in 50% water and 50% acetonitrile containing 0.1% TFA, filtered through a fritted syringe to remove the resin and lyophilized.

Peptide Purification

The peptides were redissolved in water and acetonitrile containing 0.1% TFA, filtered through a 0.22 µm nylon filter and purified by mass-directed semi-preparative reversed-phase HPLC. Solvent A was water with 0.1% TFA additive and Solvent B was acetonitrile with 0.1% TFA additive. A linear gradient that changed at a rate of 0.5%/min was used. Most of the peptides were purified on an Agilent Zorbax SB C3 column: 9.4×250 mm, 5 µm. Extremely hydrophilic peptides, such as the arginine-rich sequences were purified on an Agilent Zorbax SB C18 column: 9.4×250 mm, 5 µm. Using mass data about each fraction from the instrument, only pure fractions were pooled and lyophilized. The purity of the fraction pool was confirmed by LC-MS.

Using the protocol of Example 1, the peptides of Table 2 were synthesized.

Example 2: PMO-DBCO Synthesis

PMO IVS-654 (50 mg, 8 µmol) was dissolved in 150 µL DMSO. To the solution was added a solution containing 2 equivalents of Dibenzocyclooctyne acid (5.3 mg, 16 μmol) activated with HBTU (37.5 μL of 0.4 M HBTU in DMF, 15 μmol) and DIEA (2.8 μL, 16 μmol) in 40 μL DMF (Final reaction volume=0.23 mL). The reaction proceeded for 25 min before being quenched with 1 mL of water and 2 mL of ammonium hydroxide. The ammonium hydroxide will hydrolyze any ester formed during the course of the reaction. After 1 hour, the solution was diluted to 40 mL and purified using reversed-phase HPLC (Agilent Zorbax SB C3 column: 21.2×100 mm, 5 μm) and a linear gradient from 2 to 60% B (solvent A: water; solvent B: acetonitrile) over 58 min (1% B/min). Using mass data about each fraction from the instrument, only pure fractions were pooled and lyophilized. The purity of the fraction pool was confirmed by LC-MS.

Example 3: Library Synthesis Conditions

Reaction 1

PMO-DBCO was dissolved in water at 10 mM concentration (determined gravimetrically). The module 2 peptides were dissolved in water containing 0.1% trifluoroacetic acid at 10 mM concentration (determined gravimetrically; the molecular weight was calculated to include 0.5 trifluoroacetate counter ions per lysine, arginine, and histidine residue). In a microcentrifuge tube, 50 μL of PMO-DBCO solution was mixed with 50 μL of module 2 peptide. The solution was mixed and the reaction was allowed to proceed for one hour. Then, the product was analyzed by LC-MS and the solvent was removed by lyophilization. Lastly, the product was resuspended in 100 μL of DMSO to provide a 5 mM solution and stored at −20° C.

Reaction 2

Stock solutions were prepared by dissolving module 3 peptides and module 4 peptides in water at 10 mM concentration (determined gravimetrically). For each reaction, 4 μL of module 3 peptide was mixed with 4 μL of module 4 peptide in a PCR tube. Separately, the copper bromide solution was prepared by mixing 1 mL of degassed DMSO with 2.8 mg copper (I) bromide under $N_2$ to afford a 20 mM solution. Under ambient conditions, 4 μL of the CuBr solution was added to the mixture of module peptides 3 and 4. The reaction was capped and the reaction was allowed to proceed for 2 hours; the small amount of O2 present during reaction setup does not substantially impede reaction progress. After 2 hours, 2 μL of a 100 mM solution of $Na_2HPO_4$ was added. The PCR tube was then sonicated, vortexed, and centrifuged. To remove the solvent, the PCR tube was centrifuged under vacuum using a Savant SPD121P Speed-Vac set at 35° C. for 2 hours. Lastly, the product was resuspended in 16 μL of DMSO to provide a 5 mM solution and stored at −80° C. The product was analyzed by LC-MS.

Reaction 3

The final modular construct was synthesized through the combination of module 1-2 and module 3-4. First, 1.6 μL of reaction 2 was added to a 384-well plate. Separately, 30 μL of reaction 1 was mixed with 15 μL of TCEP solution (100 mM TCEP-HCl in 50/50 water/DMSO containing 400 mM NaOH) and 75 μL DMSO. Then, 1.6 μL of the reaction 1 solution was added to reaction 2 in the 384 well plate. Each individual reaction ultimately contained 0.4 μL of reaction 1 (at 5 mM in DMSO), 1.6 μL of reaction 2 (at 5 mM in DMSO), 0.2 μL TCEP solution (at 100 mM in water/ DMSO), and 1 μL DMSO. Excess reaction 2 was used to force the reaction to go to completion; the presence of copper hinders the efficiency of this conjugation. Reaction 1 was used as a limiting reagent to avoid excess PMO, which is the active component for the cell culture assays. The reaction was allowed to proceed for 2 hours, and then the plate was stored at −80° C. The reaction was analyzed by LC-MS.

Example 4: HeLa-654 eGFP Assay

HeLa 654 cells were maintained in MEM supplemented with 10% (v/v) fetal bovine serum (FBS) and 1% (v/v) penicillin-streptomycin at 37° C. and 5% $CO_2$. Eighteen hours prior to treatment, the cells were plated at a density of 5,000 cells per well in a 96-well plate in MEM supplemented with 10% FBS and 1% penicillin-streptomycin. The day of the experiment, the 384 well plate containing the crude reaction mixtures in DMSO was diluted to 100 μM by the addition of 16.8 μL of PBS to the 3.2 μL reaction mixture. Then, each construct was diluted to 5 μM in MEM supplemented with 10% FBS and 1% penicillin-streptomycin. Cells were incubated with each conjugate at a concentration of 5 μM for 22 hours at 37° C. and 5% $CO_2$. Next, the treatment media was aspirated the cells were incubated with Trypsin-EDTA 0.25% for 15 min at 37° C. and 5% $CO_2$, washed 1× with PBS, and resuspended in PBS with 2% FBS and 2 μg/mL propidium iodide. Flow cytometry analysis was carried out on a BD LSRII flow cytometer. Gates were applied to the data to ensure that cells that were highly positive for propidium iodide or had forward/side scatter readings that were sufficiently different from the main cell population were excluded. Each sample was capped at 5,000 gated events.

Figure 6:
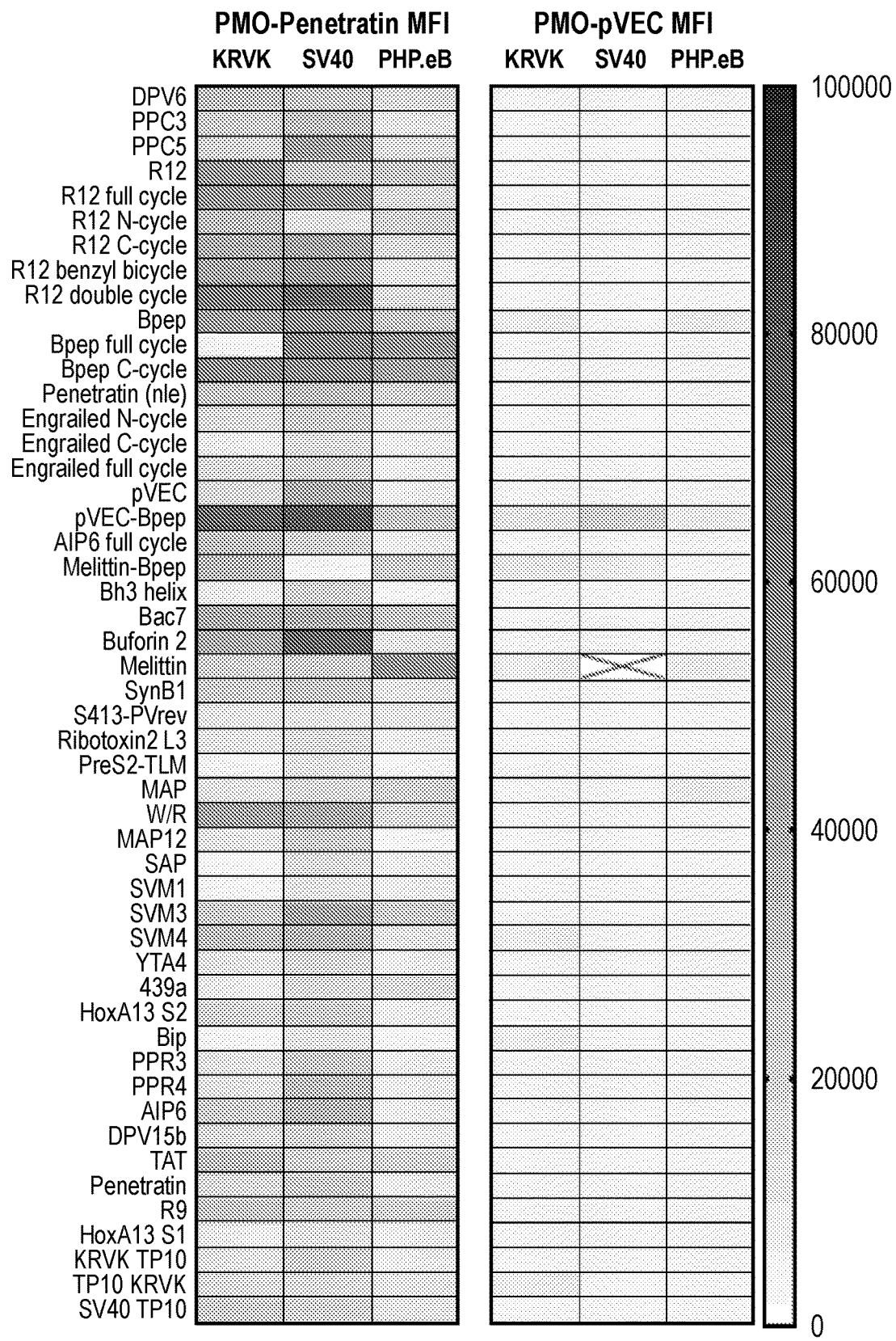
FIG. 6 shows heat maps disclosing the mean fluorescence intensity of the 600 constructs tested in the HeLa-654 assay (n=1 replicate well). Boxes marked with an "X" are constructs in which the gated cell count was zero.
Figure 6:
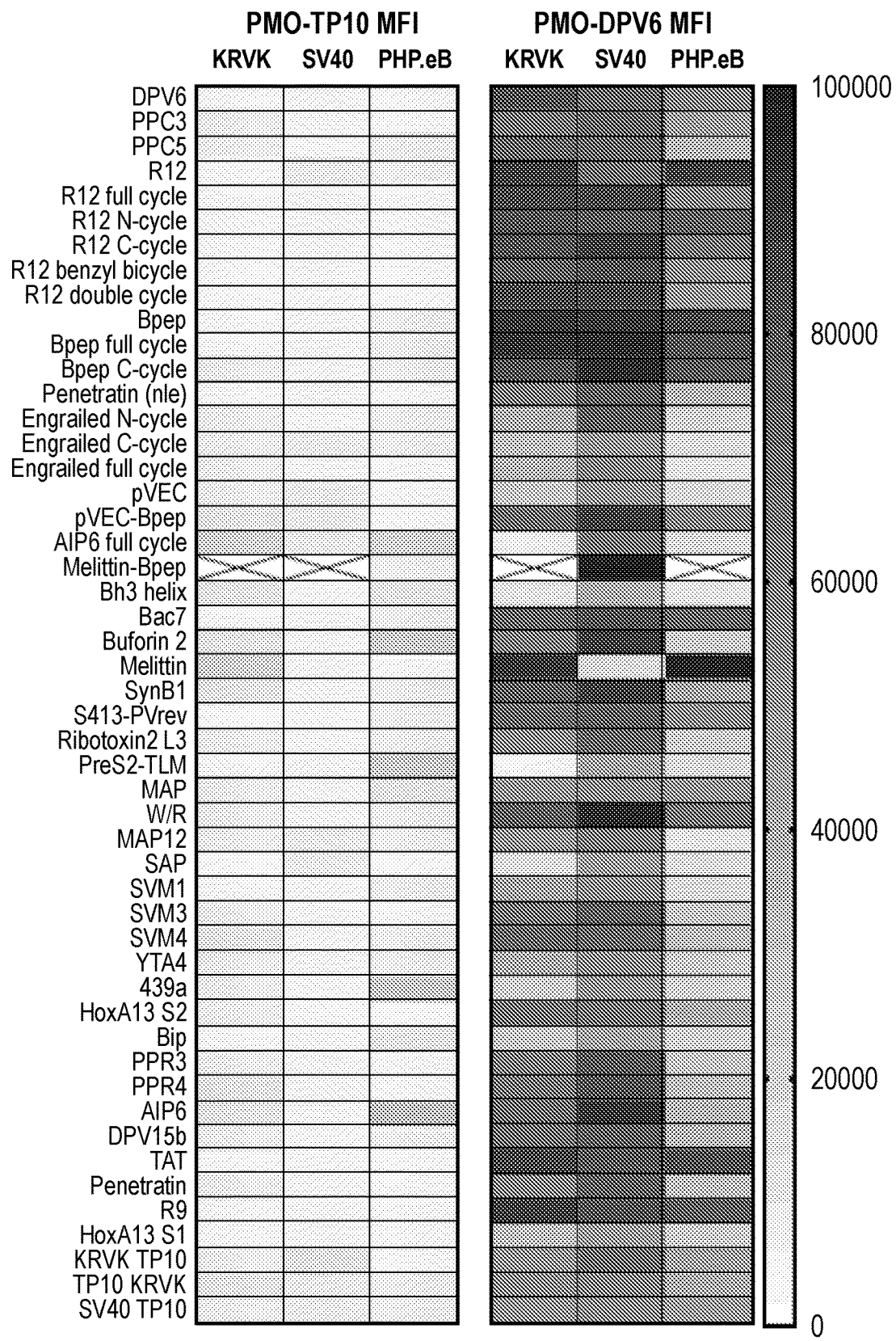
Figure 7:
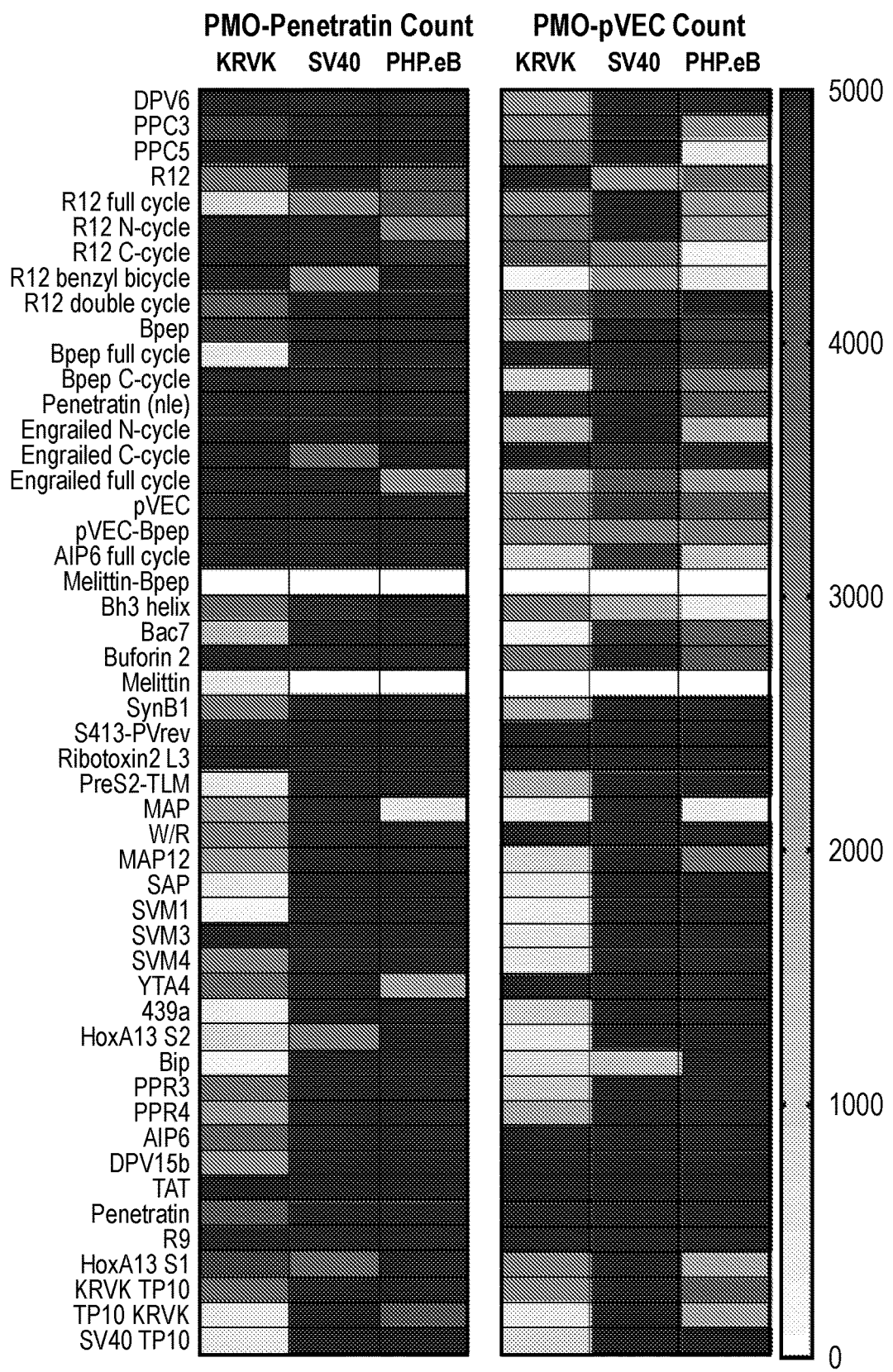
FIG. 7 shows heat maps disclosing the total cell count after treatment with 600 constructs (n=1 replicate well). The number of gated cells was capped at 5,000.
Figure 7:
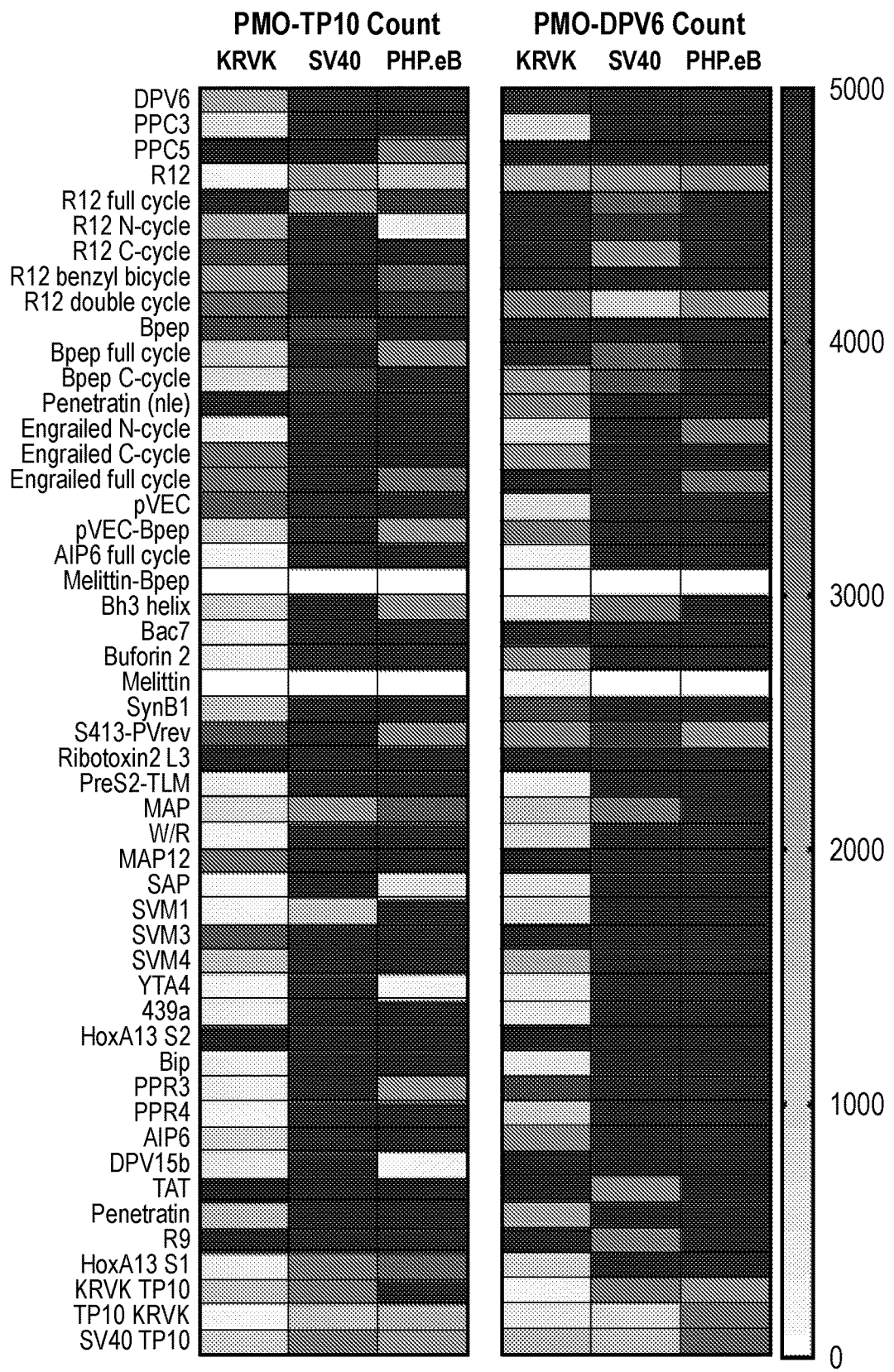

Analysis was conducted using Graphpad Prism 7. For each sample, the mean fluorescence intensity and the number of gated cells was measured (FIGS. 6 and 7) and the intensity multiplied by the cell number was calculated (FIG. 5).

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

What is claimed is:

1. A trimeric peptide-oligonucleotide conjugate of Formula I:

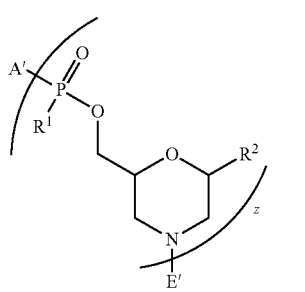

or a pharmaceutically acceptable salt thereof, wherein:

A' is selected from $—N(H)CH_2C(O)NH_2$, $—N(C_{1-6}\text{-alkyl})CH_2C(O)NH_2$,

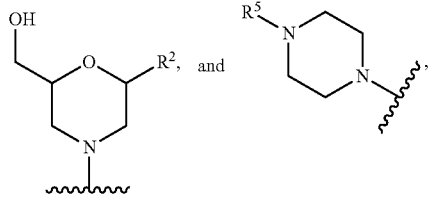

wherein $R^5$ is $—C(O)(O\text{-alkyl})_x\text{-OH}$, wherein x is 3-10 and each alkyl group is, independently at each occurrence, $C_{2-6}$-alkyl, or R⁵ is selected from —C(O)C₁₋₆-alkyl, trityl, monomethoxytrityl, —(C₁₋₆-alkyl)-R⁶, —(C₁₋₆-heteroalkyl)-R⁶, aryl-R⁶, heteroaryl-R⁶, —C(O)O—(C₁₋₆-alkyl)-R⁶, —C(O)O-aryl-R⁶, —C(O)O-heteroaryl-R⁶, and

;

wherein R⁶ is selected from OH, SH, and NH₂, or R⁶ is O, S, or NH, each of which are covalently-linked to a solid support;

each R¹ is independently selected from OH and —N(R³)(R⁴), wherein each R³ and R⁴ are, independently at each occurrence, —C₁₋₆-alkyl;

each R² is independently, at each occurrence, selected from H, a nucleobase, and a nucleobase functionalized with a chemical protecting-group, wherein the nucleobase, independently at each occurrence, comprises a C₃₋₆-heterocyclic ring selected from pyridine, pyrimidine, triazinane, purine, and deaza-purine;

z is 8-40; and

E' is selected from H, —C₁₋₆-alkyl, —C(O)C₁₋₆-alkyl, benzoyl, stearoyl, trityl, monomethoxytrityl, dimethoxytrityl, trimethoxytrityl,

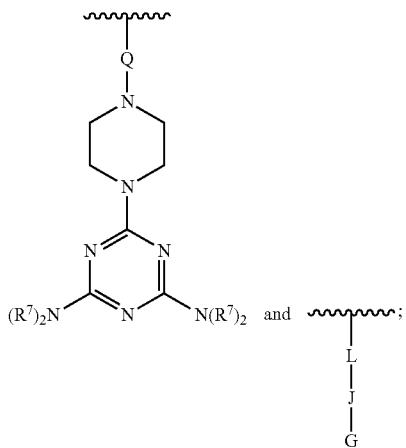

wherein

Q is —C(O)(CH₂)₆C(O)— or —C(O)(CH₂)₂S₂(CH₂)₂C(O)—;

R⁷ is —(CH₂)₂OC(O)N(R⁸)₂, wherein R³ is —(CH₂)₆NHC(=NH)NH₂;

L is —C(O)(CH₂)₁₋₆—C₇₋₁₅-heteroaromatic-(CH₂)₁₋₆C(O)—, wherein L is covalently-linked by an amide bond to the amino-terminus of J;

J is —P¹-L¹-P²-L²-P³—;

P¹, P², and P³ are each independently a cell-penetrating peptide, wherein P¹ and P² each comprise at least one terminal or internal cysteine residue, and P² comprises at least one terminal or internal lysine residue;

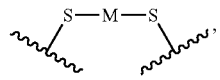

M is

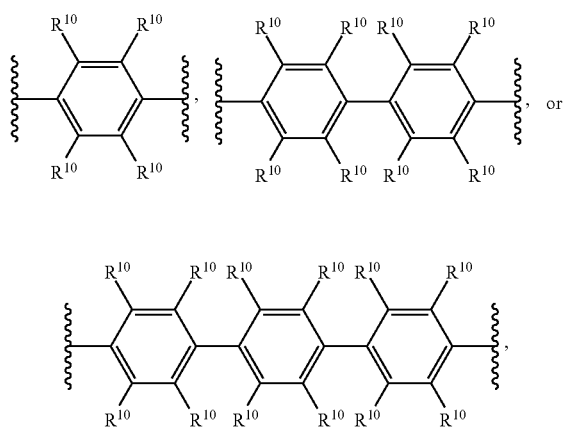

and R¹⁰ is independently at each occurrence H or a halogen, wherein L¹ is covalently-linked to the side chain of a terminal or internal cysteine of P¹ and P²;

L² is —(CH₂)₁₋₆—C₁₋₆-heteroaromatic-(CH₂)₁₋₆C(O)—, wherein L² is covalently-linked to the side chain of a terminal or internal lysine on P² and is covalently-linked by an amide bond to the amino-terminus of P³;

G is selected from H, —C(O)C₁₋₆-alkyl, benzoyl, and stearoyl, wherein G is covalently-linked via —NH— to the carboxy-terminus of J; and wherein at least one of the following conditions is true:

1)

A' is 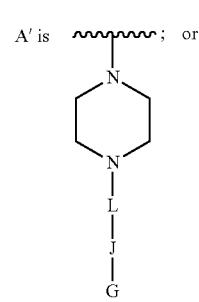 ; or

2)

E' is 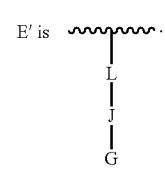 .

2. The trimeric peptide-oligonucleotide conjugate of claim 1, or a pharmaceutically acceptable salt thereof, wherein A' is

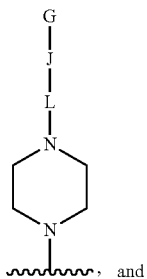, and

E' is selected from H, —C(O)CH$_3$, trityl, 4-methoxytrityl, benzoyl, and stearoyl.

3. The trimeric peptide-oligonucleotide conjugate of claim 1, or a pharmaceutically acceptable salt thereof, wherein the peptide-oligonucleotide conjugate of Formula I is a peptide-oligonucleotide conjugate selected from:

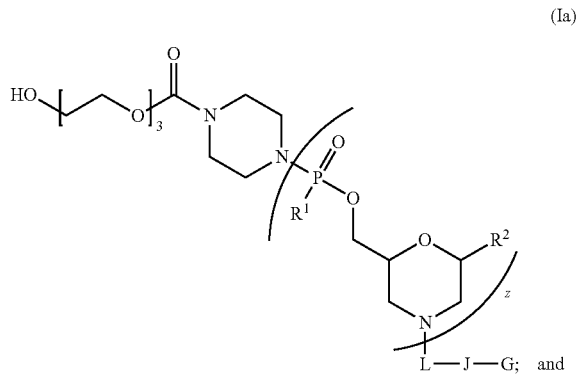

(Ia)

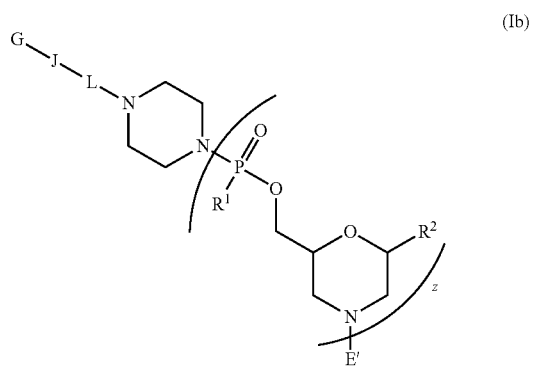

(Ib)

wherein E' is selected from H, C$_{1-6}$-alkyl, —C(O)CH$_3$, benzoyl, and stearoyl.

4. The trimeric peptide-oligonucleotide conjugate of claim 1, or a pharmaceutically acceptable salt thereof, wherein each of the cell-penetrating peptides are independently an amphipathic peptide, a nuclear targeting peptide, an endosomal disrupting peptide, a chimeric peptide, a cyclic peptide, a bicyclic peptide, or an oligoarginine peptide.

5. The trimeric peptide-oligonucleotide conjugate of claim 1, or a pharmaceutically acceptable salt thereof, wherein P$^1$ is an amphipathic peptide.

6. The trimeric peptide-oligonucleotide conjugate of claim 1, or a pharmaceutically acceptable salt thereof, wherein P$^2$ is a nuclear targeting peptide.

7. The trimeric peptide-oligonucleotide conjugate of claim 5, or a pharmaceutically acceptable salt thereof, wherein the amphipathic peptide comprises a hydrophobic peptidyl segment and a hydrophilic peptidyl segment, wherein the hydrophobic peptidyl segment comprises a sequence of 2 to 10 amino acids independently selected from glycine, isoleucine, alanine, valine, leucine, phenylalanine, tyrosine, or tryptophan, and wherein the hydrophilic peptidyl segment comprises a sequence of 2-20 amino acids independently selected from charged amino acids, uncharged but polar amino acids, or hydrophobic amino acids, wherein the hydrophilic peptidyl segment comprises at least one non-hydrophobic amino acid.

8. The trimeric peptide-oligonucleotide conjugate of claim 7, or a pharmaceutically acceptable salt thereof, wherein the hydrophilic peptidyl segment comprises a sequence of 2 to 20 amino acids independently selected from arginine, lysine, glutamine, asparagine, histidine, serine, threonine, tryptophan, alanine, isoleucine, leucine, methionine, phenylalanine, valine, proline, or glycine, wherein the hydrophilic peptidyl segment comprises at least one non-hydrophobic amino acid.

9. The trimeric peptide-oligonucleotide conjugate of claim 1, or a pharmaceutically acceptable salt thereof, wherein P$^1$ is Penetratin (SEQ ID NO: 45), pVEC (SEQ ID NO: 17), TP10 (SEQ ID NO: 52), or DPV6 (SEQ ID NO: 1).

10. The trimeric peptide-oligonucleotide conjugate of claim 1, or a pharmaceutically acceptable salt thereof, wherein P$^2$ is KRVK (SEQ ID NO: 50), SV40 (SEQ ID NO: 53), or AAV-PHP.eB (SEQ ID NO: 54).

11. The trimeric peptide-oligonucleotide conjugate of claim 1, or a pharmaceutically acceptable salt thereof, wherein P$^3$ is DPV6 (SEQ ID NO: 1), PPC3 (SEQ ID NO: 2), PPC5 (SEQ ID NO: 3), R12 (SEQ ID NO: 4), R12 full cycle (SEQ ID NO: 5), R12 N-cycle (SEQ ID NO: 6), R12 C-cycle (SEQ ID NO: 7), R12 benzyl bicycle (SEQ ID NO: 8), R12 double cycle (SEQ ID NO: 9), Bpep (SEQ ID NO: 10), Bpep full cycle (SEQ ID NO: 11), Bpep C-cycle (SEQ ID NO: 12), Penetratin (nle) (SEQ ID NO: 13), Engrailed N-cycle (SEQ ID NO: 14), Engrailed C-cycle (SEQ ID NO: 15), Engrailed full cycle (SEQ ID NO: 16), pVEC (SEQ ID NO: 17), pVEC-Bpep (SEQ ID NO: 18), AIP6 full cycle (SEQ ID NO: 19), Melittin-Bpep (SEQ ID NO: 20), Bh3 helix (SEQ ID NO: 21), Bac7 (SEQ ID NO: 22), Buforin 2 (SEQ ID NO: 23), Melittin (SEQ ID NO: 24), SynB1 (SEQ ID NO: 25), S413-PVrev (SEQ ID NO: 26), Ribotoxin2 L3 (SEQ ID NO: 27), PreS2-TLM (SEQ ID NO: 28), MAP (SEQ ID NO: 29), W/R (SEQ ID NO: 30), MAP12 (SEQ ID NO 31), SAP (SEQ ID NO: 32), SVM1 (SEQ ID NO: 33), SVM3 (SEQ ID NO: 34), SVM4 (SEQ ID NO: 35), YTA4 (SEQ ID NO: 36), 439a (SEQ ID NO: 37), HoxA13 serine2 (SEQ ID NO: 38), Bip (SEQ ID NO: 39), PPR3 (SEQ ID NO: 40), PPR4 (SEQ ID NO 41), AIP6 (SEQ ID NO: 42), DPV15b (SEQ ID NO: 43), TAT (SEQ ID NO: 44), Penetratin (SEQ ID NO: 45), R9 (SEQ ID NO: 46), HoxA13 serine1 (SEQ ID NO: 47), KRVK TP10 (SEQ ID NO: 48), TP10 KRVK (SEQ ID NO: 49), or SV40 TP10 (SEQ ID NO: 51).

12. The trimeric peptide-oligonucleotide conjugate of claim 1, or a pharmaceutically acceptable salt thereof, wherein P$^1$ is DPV6 (SEQ ID NO: 1).

13. The trimeric peptide-oligonucleotide conjugate of claim 1, or a pharmaceutically acceptable salt thereof, wherein P$^3$ is DPV6 (SEQ ID NO: 1), Bpep (SEQ ID NO: 10), pVEC-Bpep (SEQ ID NO: 18), Buforin 2 (SEQ ID NO: 23), SynB1 (SEQ ID NO: 25), W/R (SEQ ID NO: 30), or AIP6 (SEQ ID NO: 46).

14. The trimeric peptide-oligonucleotide conjugate of claim 1, or a pharmaceutically acceptable salt thereof, wherein P$^1$ is DPV6 (SEQ ID NO: 1), P$^2$ is SV40 (SEQ ID NO: 53), and P³ is DPV6 (SEQ ID NO: 1), Bpep (SEQ ID NO: 10), pVEC-Bpep (SEQ ID NO: 18), Buforin 2 (SEQ ID NO 23), SynB1 (SEQ ID NO: 25), W/R (SEQ ID NO: 30), or AIP6 (SEQ ID NO: 46).

15. The trimeric peptide-oligonucleotide conjugate of claim 1, or a pharmaceutically acceptable salt thereof, wherein P¹ is DPV6 (SEQ ID NO: 1), P² is SV40 (SEQ ID NO: 53), and P³ is pVEC-Bpep (SEQ ID NO: 18).

16. The trimeric peptide-oligonucleotide conjugate of claim 1, or a pharmaceutically acceptable salt thereof, wherein P¹ is DPV6 (SEQ ID NO: 1), P² is SV40 (SEQ ID NO: 30), and P³ is W/R (SEQ ID NO: 30).

17. The trimeric peptide-oligonucleotide conjugate of claim 1, or a pharmaceutically acceptable salt thereof, wherein P¹ is DPV6 (SEQ ID NO: 1), P² is SV40 (SEQ ID NO: 30), and P³ is SynB1 (SEQ ID NO: 25).

18. The trimeric peptide-oligonucleotide conjugate of claim 1, or a pharmaceutically acceptable salt thereof, wherein each R¹ is N(CH₃)₂.

19. The trimeric peptide-oligonucleotide conjugate of claim 1, or a pharmaceutically acceptable salt thereof, wherein L is

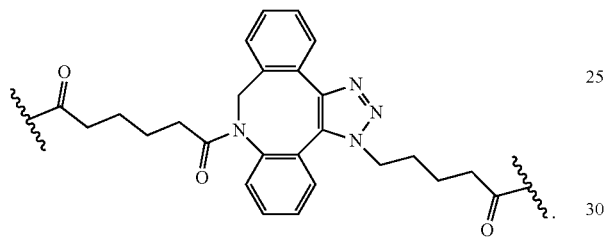

20. The trimeric peptide-oligonucleotide conjugate of claim 1, or a pharmaceutically acceptable salt thereof, wherein
M is

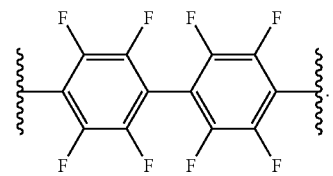 [SMILES: *c1c(F)c(F)c(-c2c(F)c(F)c(*)c(F)c2F)c(F)c1F]

21. The trimeric peptide-oligonucleotide conjugate of claim 1, or a pharmaceutically acceptable salt thereof, wherein L¹ is covalently-linked to the side chain of a terminal cysteine on P¹ and P² to form the structure:

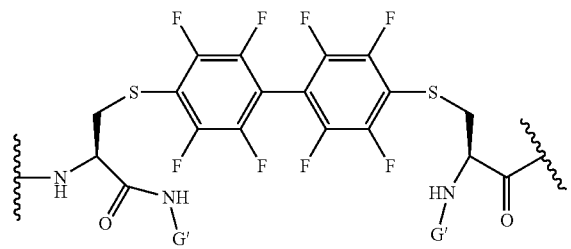

wherein
G' is selected from H, —C(O)C₁₋₆-alkyl, benzoyl, and stearoyl.

22. The trimeric peptide-oligonucleotide conjugate of claim 1, or a pharmaceutically acceptable salt thereof, wherein L² is covalently-linked to the side chain of a terminal lysine on P² and is covalently-linked by an amide bond to the amino-terminus of P³ to form the structure:

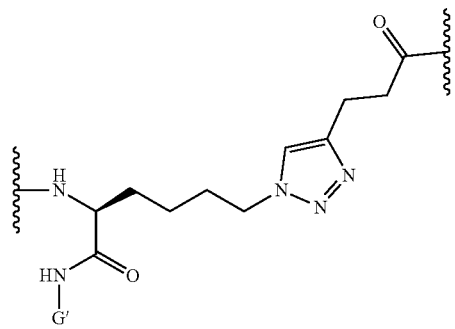

wherein
G' is selected from H, —C(O)C₁₋₆-alkyl, benzoyl, and stearoyl.

23. The trimeric peptide-oligonucleotide conjugate of claim 1, or a pharmaceutically acceptable salt thereof, having the structure:

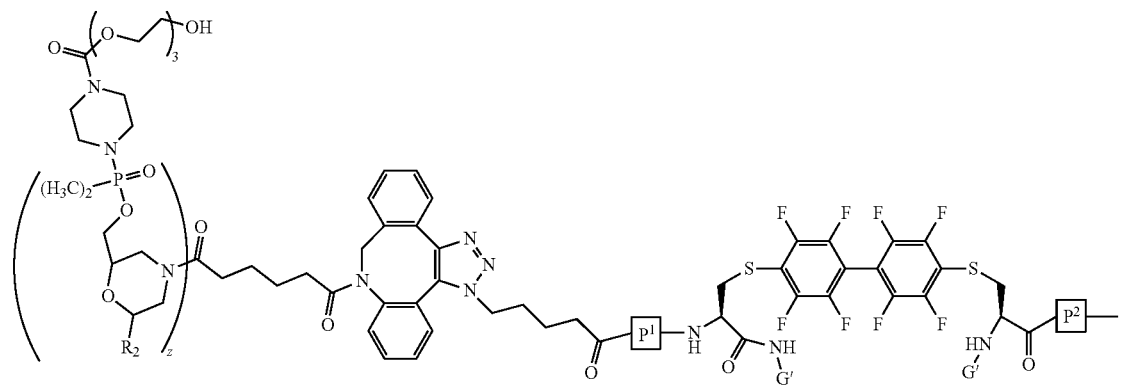

-continued
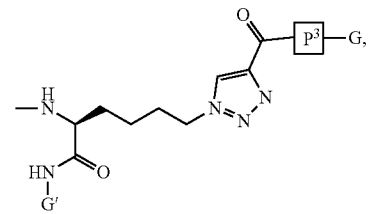
wherein
each R² is a nucleobase;
G is H;
each G' is H;
P¹ is DPV6 (SEQ ID NO: 1);
P² is SV40 (SEQ ID NO: 53); and
P³ is W/R (SEQ ID NO: 30).
* * * * *